(12) United States Patent
Dantsker et al.

(10) Patent No.: US 10,025,905 B2
(45) Date of Patent: Jul. 17, 2018

(54) COMMUNICATION DEVICE RESOURCE ALLOCATION BASED ON MEDICAL DATA CRITICALITY AND RESOURCE STATUS

(71) Applicant: QUALCOMM Incorporated, San Diego, CA (US)

(72) Inventors: Eugene Dantsker, San Diego, CA (US); Aiman Albert Abdel-Malek, La Jolla, CA (US); Rajeev Durai Rajan, San Diego, CA (US); Donald Jones, Cardiff By The Sea, CA (US); Muhammed Ibrahim Sezan, Los Gatos, CA (US); Leonid Sheynblat, Hillsborough, CA (US)

(73) Assignee: QUALCOMM Incorporated, San Diego, CA (US)

( * ) Notice: Subject to any disclaimer, the term of this patent is extended or adjusted under 35 U.S.C. 154(b) by 305 days.

(21) Appl. No.: 14/252,565

(22) Filed: Apr. 14, 2014

(65) Prior Publication Data

US 2015/0066538 A1    Mar. 5, 2015

Related U.S. Application Data

(60) Provisional application No. 61/873,155, filed on Sep. 3, 2013.

(51) Int. Cl.
| | |
|---|---|
| *G06F 19/00* | (2018.01) |
| *G16H 40/63* | (2018.01) |
| *G16H 10/60* | (2018.01) |

(52) U.S. Cl.
CPC ...... *G06F 19/3406* (2013.01); *G06F 19/3418* (2013.01); *G16H 10/60* (2018.01); *G16H 40/63* (2018.01)

(58) Field of Classification Search
CPC ............... G06F 19/3406; G06F 19/322; G06F 19/3418; A61N 1/37282; G16H 40/63
(Continued)

(56) References Cited

U.S. PATENT DOCUMENTS

| | | |
|---|---|---|
| 2,765,283 A | 10/1956 | Sacken |
| 6,906,998 B1 | 6/2005 | Mujeeb et al. |

(Continued)

FOREIGN PATENT DOCUMENTS

| | | |
|---|---|---|
| EP | 2280344 A1 | 2/2011 |
| WO | 2013083022 A1 | 6/2013 |

OTHER PUBLICATIONS

Varshney U., "Pervasive Healthcare and Wireless Health Monitoring," Mobile Networks and Applications, 2007, vol. 12 (2-3), pp. 113-127.

(Continued)

*Primary Examiner* — Hiep Van Nguyen
(74) *Attorney, Agent, or Firm* — The Marbury Law Group

(57) ABSTRACT

Methods and devices are disclosed for managing a resource of a communication device configured to process and communicate medical data in addition to other data. The systems and devices may implement the method, including determining whether to switch to a medical mode based on at least one signal. In response to determining to switch to the medical mode, the communication device may be switched to the medical mode. A resource status associated with a plurality of resources used by the communication device may be weighed against a medical data criticality associated with the medical data managed by the communication device. The method may include allocating a resource of the plurality of resources on a sliding priority scale. The allocating may include allocating a resource of the plurality of (Continued)

resources preferentially to the medical data over the other data.

30 Claims, 7 Drawing Sheets

(58) Field of Classification Search
USPC .............................................................. 705/3
See application file for complete search history.

(56) References Cited

U.S. PATENT DOCUMENTS

| | | | |
|---|---|---|---|
| 7,292,956 B1 | 11/2007 | Guday et al. | |
| 8,265,556 B2 * | 9/2012 | Tekin | A61B 5/0022 455/41.1 |
| 8,285,560 B2 | 10/2012 | Gopinathan et al. | |
| 8,373,556 B2 * | 2/2013 | LaLonde | A61N 1/37282 340/3.1 |
| 8,395,498 B2 * | 3/2013 | Gaskill | A61N 1/37282 340/5.61 |
| 8,456,997 B2 | 6/2013 | Soomro | |
| 2009/0063193 A1 * | 3/2009 | Barton | A61N 1/37282 705/3 |
| 2012/0057486 A1 | 3/2012 | Abedi et al. | |
| 2012/0253847 A1 | 10/2012 | Dell'Anno et al. | |

OTHER PUBLICATIONS

International Search Report and Written Opinion—PCT/US2014/053297—ISA/EPO—Jan. 22, 2015.

* cited by examiner

COMMUNICATION DEVICE RESOURCE ALLOCATION BASED ON MEDICAL DATA CRITICALITY AND RESOURCE STATUS

RELATED APPLICATIONS

This application is a non-provisional application of U.S. Provisional Application No. 61/873,155 filed Sep. 3, 2013 entitled "Mobile Communication Device Resource Allocation Based On Medical Data Criticality and Resource Status," the entire contents of which are hereby incorporated by reference for all purposes.

BACKGROUND

Contemporary communication devices, such as smart phones or feature phones, perform various functions that are not specific to interfacing with or managing medical data. Also, such communication devices are generally equipped with various resources needed to perform functions for which they were designed. Such resources may include a power source (e.g., a battery), radios (cellular, GPS, Wi-Fi, Bluetooth®, etc.), processors, internal functions (e.g., applications), memory, sensors, display(s), interfaces, peripherals and remote network elements available to the communication device. Resources may be shared to execute various functions of the device. For instance with a cellular telephone, text messages sent via short message services (SMS) may arrive during a voice call, where both functions share the cellular antenna, a central processor and a battery. Similarly, the communication device may share resources while performing GPS tracking and maintaining a video streaming session. When resource usage conflicts arise between different functions of the communication device those shared resources may be strained, which may impact performance. Additionally, when the communication device has multiple tasks to complete but not enough of a given resource to complete them all, it may simply complete tasks on a first come first serve basis. Also, when battery power runs low, communication device resource management systems may allocate resource based on predefined resource priorities. Consequently, conventional communication devices are not well suited to support many medical applications.

SUMMARY

The various embodiments include methods, systems and devices for managing a resource of a communication device configured to process and communicate medical data in addition to other data. The systems and devices may implement the method, including determining whether to switch to a medical mode based on at least one signal. In response to determining to switch to the medical mode, the communication device may be switched to the medical mode. A resource status associated with a plurality of resources used by the communication device may be weighed against a medical data criticality associated with the medical data managed by the communication device. The method may include allocating a resource of the plurality of resources on a sliding priority scale. The allocating may include allocating a resource of the plurality of resources preferentially to the medical data over other data.

Further embodiments may include the at least one signal being one of an on-signal and an off signal. In addition, the at least one signal may be one of an always on-signal and an always off-signal. Also, determining whether to switch may be based on one of a manual control, a first processor control that automatically switches into the medical mode or a regular mode based on input from the plurality of resources, a second processor control that switches into the medical mode or the regular mode based on signaling from the plurality of resources, and a factory setting. Weighing a resource status may be performed by a remote resource separate from the communication device.

Further embodiments may include allocating the plurality of resources in various ways. At least a first part of the medical data may be diverted to a first onboard resource of the communication device. In addition, at least a second part of the medical data may be diverted from a second onboard resource to a remote resource of the communication device. A predetermined portion of use of the resource may be ensured as being available for managing the medical data. In addition, the medical data may be given precedence over the other data with regard to the use of a third onboard resource of the communication device. The resource may be dedicated exclusively to managing the medical data and prevented from being used for other data. Medical data may be diverted to the resource when the resource is a dedicated resource used exclusively for managing the medical data. Also, the plurality of resources may be prevented from being used for managing other data.

Further embodiments may include a communication device having one or more dedicated resources, which may be activated in response to the device switching to the medical mode in which the dedicated resource is used for the medical data and restricted from being used for other data. Such dedicated resources may be in the form of a medical mode processor, a medical mode memory, and/or a medical mode transceiver or modem that are dedicated to and used exclusively for processing, analyzing, storing and/or transmitting medical-related data. Also, a resource of the communication device or the communication device itself may be a system on chip (SOC), or even a medical grade SOC. In this way, a memory, a modem, sensor interfaces, and processor configured with software instructions to perform operations of various embodiments may be coupled and integrated together on a SOC. In addition, at least one of a radio and a power source may be integrated on the SOC.

Further embodiments may include systems and devices implementing a method including receiving, at an inference engine of the communication device, a plurality of data associated with a user's condition. A medical data criticality may be determined by combining the plurality of data, and a resource allocation may be determined based at least in part on the determined medical data criticality. The plurality of data may include at least two different types of data. Also, the plurality of data may include at least one of environmental data, context data, physiological and biological data, health record data, long-term historical health data, directly input data, individual health risk data, personal genomic data, behavioral data, and public alerts.

In further embodiments, determining the medical data criticality may include generating a criticality indicator corresponding to the medical data criticality. Generating the criticality indicator may include comparing long-term historical health data associated with a patient with at least one temporal characteristic obtained from a sensor attached to a user. When a change is detected in the at least one temporal characteristic, the criticality indicator may be changed from a default low value to a high value. Further, the criticality indicator may be provided to an onboard or remote resource of the communication device. The resource allocation determination may include generating an indication of at least one action to be taken. A necessary resource for completing at least one action during a particular period of time may be determined. Thus, a resource allocation in a medical mode may be determined based on the determined necessary resource. Information associated with the medical data criticality may be exchanged with at least one of a clinical decision support system and a knowledge support system. Also, at least one of determining the medical data criticality or determining the resource allocation may be performed using a state machine.

In further embodiments, a dedicated processor, memory and modem, in addition to other circuitry, may be implemented as an SOC or a dedicated medical mode SOC that may be implemented in any device in order give it medical mode capabilities. Such a medical mode SOC may also include processor-executable instructions for configuring its processor to execute one or more of the embodiment methods of operating in a condition-appropriate medical mode, including allocating resources of a device in which the SOC is installed as described herein. Such an SOC may even include a dedicated back up power supply, such as a small rechargeable battery. This embodiment enables a wide variety of devices to be configured with a medical mode capability/functionality simply by including the SOC in the device's circuitry. This embodiment also enables protection of medical data by storing such information within the dedicated memory, which may be encrypted or isolated from the rest of the device circuitry via the SOC architecture in order to meet privacy standards/requirements and/or government regulations (e.g., U.S. Health Insurance Portability and Accountability Act (HIPAA) compliance). Implementing such an embodiment dedicated medical mode SOC in a communication device also provides the dedicated processing, memory, communication and other resources that may be necessary to meet or comply with government standards of safety, reliability and traceability as may be required to meeting government-licensing requirements established for medical equipment. By implementing the regulatory-compliance related components and software in an integrated SOC, this embodiment may simplify the design, production and licensing of communication devices that can perform regulated medical-related functions (e.g., monitoring and reporting of medical-related sensors and conditions).

Further embodiments may include a communication device having a processor configured with processor-executable software instructions to perform various operations corresponding to the methods discussed above.

Further embodiments may include a communication device having various means for performing functions corresponding to the method operations discussed above.

Further embodiments may include a non-transitory processor-readable storage medium having stored thereon processor-executable instructions configured to cause a processor of a communication device to perform various operations corresponding to the method operations discussed above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
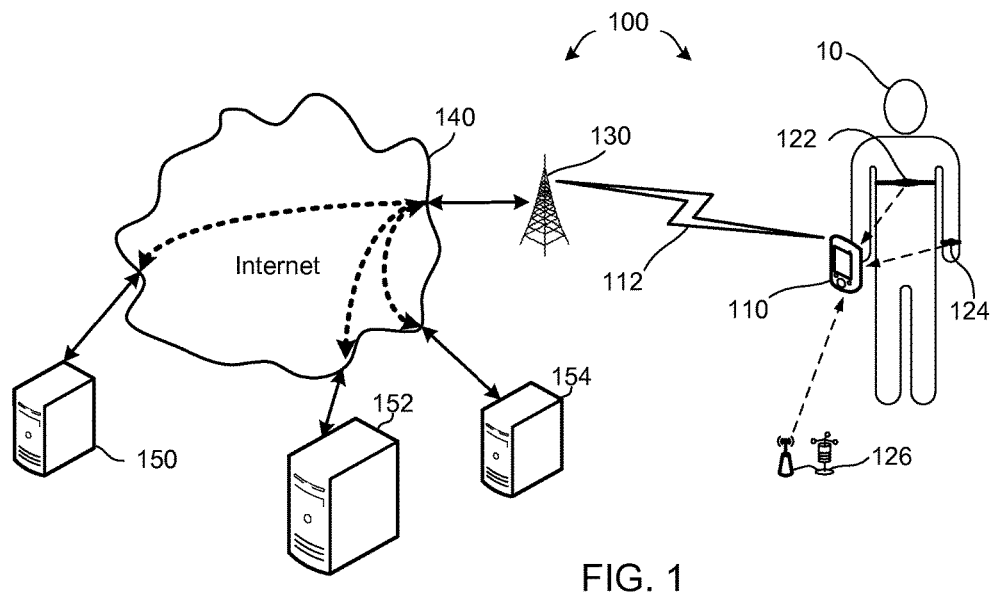
FIG. 1 is a communication system block diagram illustrating functionality of various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims. Alternate embodiments may be devised without departing from the scope of the disclosure. Additionally, well-known elements of the disclosure will not be described in detail or will be omitted so as not to obscure the relevant details of the disclosure.

The terms "communication device" or "electronic device" are used interchangeably to refer to any electronic device, such as any one or all of cellular telephones, smart phones, personal or mobile multi-media players, personal data assistants, laptop computers, personal computers, tablet computers, smart books, palm-top computers, wireless electronic mail receivers, multimedia Internet enabled cellular telephones, appliances, medical devices, wireless sensors or data collectors (e.g., glucose meters, blood pressure sensors, pulse sensors, pacemakers, accelerometers, weather/atmospheric sensors, or sensors for monitoring a user's condition and/or well being), and similar personal electronic devices that include a programmable processor, memory and circuitry for establishing wireless communication pathways and transmitting/receiving data via wireless communication pathways to mobile communication networks, several examples of which are described further herein. In addition, the terms "communication device" or "electronic device," as used herein may refer to a distinct sub-system, such as particular embedded circuitry (e.g., an SOC) or component of a larger system, configured to operate as a dedicated resource or more generally as part of the larger system.

The terms "medical mode" and "medical mode of operation" are used herein interchangeably to refer to a state of operation in which a communication device is configured to receive one or more inputs and determine the appropriate resource allocation based on the one or more inputs. The one or more inputs may include a degree of criticality of the data that the communication device is processing and communicating, and an input that quantifies resources that are available to the communication device for processing and communicating that data. In some embodiments, the communication device may allocate one or more resources preferentially to process and/or communicate medical data over other data. A communication device can determine whether to switch to a medical mode, from normal mode, in a number of ways. For example, the communication device can determine to switch to the medical mode based on a manual control (e.g., a user input entered manually through a user interface). As another example, the communication device is hardwired into either the normal or the medical mode by a factory setting. As yet another example, the communication device can determine to switch to the medical mode based on one or more automatic inputs (e.g., contextual information obtained from the environment). As a further example, the communication device can determine to switch to the medical mode based on at least one signal received from one or more resources (e.g., an input signal from an onboard resource, remote resource, or from a healthcare provider entered either manually or through signaling). In medical mode, the communication device may weigh the medical data criticality against a resource status in order to determine a resource allocation along a sliding scale. The sliding scale may include conditions from one end at which resources are dedicated to processing and/or communicating medical data (i.e., "high criticality mode") to another end at which resources are not preferentially dedicated to processing and/or communicating medical data (i.e., "non-critical mode").

The term "medical data" is used herein to refer to medical and/or healthcare information represented by quantities, characters, or symbols which may be stored in a non-transitory processor-readable storage medium and on which operations may be performed by a processor. Medical data relates to information pertinent to health, healthcare, wellness, fitness, and the science of medicine or to the treatment of illness or injuries, and particularly refers to medical information associated with a particular user of a communication device. It also relates to environmental information such as air quality, temperature and humidity that is relevant to user's condition and may directly impact user's medical wellness, e.g., air quality impacting an asthma patient and air temperature impacting a patient with chronic heart disease. Medical data may also include information about the context and location of the patient, including information about patient's current geographical location or activity (e.g., standing up, walking, or falling). Medical data may include user's health records as well as user's long-term medical data measured and stored in the cloud and/or in the communication device such as daily average blood pressure values, average heart rate, average daily energy expenditure, and heart rate variability. Direct directives and inputs from medical professionals and caregivers responsible from the health of the user are also considered as medical data of the user of the communication device. Information of interest to medical practitioners regarding the health and/or wellness of a patient represented by medical data managed with a communication device may be considered medical data. Also, any data used in connection with a communication device that is not considered medical data is referred to herein as "other data." Further, the expressions "managing medical data," "manage medical data" and "management of medical data" are used herein to refer to the administration and regulation of medical data, such as through delivery, acquisition, streaming, storage, processing and/or data control.

The term "medical data criticality" is used herein to refer to information within the medical data managed by the communication device indicating a level of importance of that medical data. That level of importance may be measured by a value attributed to elements of medical data, which value is referred to herein as a "criticality indicator." Criticality indicators may be identified in medical data as direct criticality indicators (i.e., immediately apparent) or indirect criticality indicators (i.e., one needing an intermediate computation or analysis). A direct criticality indicator or indication may be in the form of a code, flag, or other form of signal that is designated to reflect the importance of the associated medical data in the form of a value. An indirect criticality indicator or indication may represent one or more variable elements of medical data that may be correlated to predefined values used to measure the associated medical data. Also, indirect criticality indicators may also need to be compared, correlated or analyzed along with other information before a value may be determined. For example, physiological or biological medical information may be combined with other information such as time of day, time of year, location, activity, specific medical readings, or previous health history, in determining a value of indirect criticality indicators identified in medical data. The criticality indicator may provide a weighting of the measured medical data that may be used along with a weighting given to the resource status in determining whether a medical data criticality exists or how resources should or may be allocated.

The term "critical resource constraint" is used herein to refer to levels of resource constraint that may impair or threaten to impair the processing or communication of medical data by a communication device. A resource constraint refers to a state of a resource of a communication device being limited or restricted from performing at least one action. The state of a resource may be measured by a resource status, which includes one or more constraint values reflecting or quantifying the extent of the constraint. The resource status may provide a weighting of the available resource(s) that may be used along with a weighting given to the criticality indicator in determining whether a critical resource constraint exists or how resources should or may be allocated.

As used herein, in connection with a communication device the terms "resource" or "device resource" are used interchangeably to refer to hardware, software and/or any other asset that may be used by the communication device. Resources may include remote resources and/or onboard resources. Remote resources refer to hardware physically separate from the communication device or software executed or partially executed by a processor physically separate from the communication device. Onboard resources refer to hardware physically joined with the communication device or software executed or partially executed on an onboard processor or component of the communication device. A resource, whether remote or onboard, may be at least one of a power source, a processor, a function (e.g., a software process), memory, a radio, communication ports, a wireless network with certain data capacity, an input device (e.g., a sensor, keyboard, buttons or touch-screen) or an output device (e.g., a display or speakers) available to the communication device. For example, resources include processor, memory, power, network, security, and privacy resources. Processor and memory resources may include computational hardware and software; network resources may include connection to a wireless network and available network resources; power resources may include available battery power; and security resources may include encryption/decryption capabilities and secure trust zones that are not accessible by the high-level operating system, and secure memories to store private data. For example, if network connection is suddenly lost, the communication device may start temporarily storing an electrocardiogram (EKG) data in the local device rather than securely transmitting it to a remote server. At that instance when network resources are scarce, the system will need to allocate memory and security resources, i.e., an encrypted memory portion for storing the EKG data and any personally identifiable information, where that part of the memory cannot be accessed, e.g., by high level operating system. Such memory may be dedicated exclusively for medical data.

The various embodiments may assist with conserving and optimizing resource availability within a communication device for transmission, processing, generation, and/or storage of medical data. Indications from resources and medical data associated with the communication device may be used to determine resource allocation, and give medical data priority over other data in response thereto. Giving medical data priority may enable multipurpose communication devices to be used to perform medical-related functions that may be of critical importance to a patient. The systems, methods, and devices of the various embodiments enable managing one or more resources of a communication device configured to appropriately prioritize medical data over other data.

Communication devices, such as smartphones and tablets, are sophisticated computing and communication platforms that can perform a variety of functions. Using a communication device as a hub for processing and routing medical data may be particularly useful to medical practitioners, patients, and medical facilities. However, contemporary resource allocation algorithms for communication devices do not discriminate, based on the type of data handled, among the functions they perform. Thus, communication devices using current resource allocation systems are incompatible with diagnostic equipment communicating important medical data.

For example, if a smartphone is used as a sensor or a hub for sensors transmitting medical data, and connectivity is limited, a conventional communication device would interrupt transmission of such data when an incoming phone call is received, regardless of the relative importance of either that medical data or the phone call. There may be circumstances, however, when communicating medical data is more important than sending or receiving other types of data. Thus, government agencies generally regulate the use of smartphone applications for transmission and/or processing of critical medical data because contemporary resource allocation algorithms do not give priority to the transmission and/or processing of medical data over non-medical data.

Consider the example of a tablet computer equipped with a wireless radio and interfaced to a patient-worn electrocardiogram (EKG) monitor. That tablet computer could be configured to continuously stream EKG data to a medical provider or remote monitoring service. An interruption in that continuous data stream due to an action of a resource management algorithm, regardless of the EKG readings, may trigger an unnecessary alert to a medical provider. Also, even without a complete interruption, the streaming medical data may compete for resources with other data of the communication device, and thus potentially experience limited power, limited connectivity, or limited processor availability. This illustrates an example of a critical resource constraint on the availability of a resource for the handling of medical data.

FIG. 1 illustrates resources that may be available to a communication device 110 through a communication system 100. The communication device 110 may be configured to manage medical data and non-medical data, in accordance with the various embodiments. In managing medical data and/or non-medical data, the communication device 110 may process/store medical data with onboard resources or have access to remote resources, such as local peripheral devices and/or remote network resources, through wired or wireless connections. FIG. 1 includes various examples of remote resources in relationship to a communication device 110.

Local peripheral devices may be remote resources in close proximity to the communication device 110, which may be connected by wired or short-range wireless connections (e.g., via USB, FireWire, Bluetooth®, ANT+®, Zigbee®, etc.). Peripheral devices generally communicate directly with the communication device, without going through an intermediate communication network. Also, peripheral devices are distinguished from onboard resources since although they may be coupled to the communication device 110 through a wired connection; the peripherals are generally spaced apart from the communication device.

The peripheral devices may include components worn by the user 10, like a heart rate monitor 122 or wrist-worn device 124, or nearby components communicating directly with the communication device 110, like weather sensor 126. Additional peripheral devices may be available as resources of the communication device 110. For example, peripheral devices may further include a blood pressure monitor, a pulse meter, a thermometer (such as a skin temperature meter), a cardiac monitor, a glucose meter, a camera connected and virtually any device associated with collecting, communicating, storing or processing medically relevant data. Additionally, peripheral devices may include sources of additional or supplemental memory, processors, power, communications and more. As with any resource, peripheral devices may maintain and/or transmit to the connected communication device a medical mode override or a constraint value, which may be used to determine whether communication device 110 needs to switch to a medical mode. In addition, the peripheral devices, as resources of the communication device 100, may receive controls or inputs from the communication device, such as part of a resource allocation.

Remote network resources may be available to the communication device 110 through a long-range wireless connection, such as cellular communications, or combinations of connections, such as a local router providing access to the internet. Cellular connections enable the communication device to communicate via signals 112 to one or more base stations 130. Such base stations 130 may in-turn be coupled to the Internet 140, providing the communication device 110 with access to any number of remote network resources. Alternatively, remote network resources may be available through wired connection(s) providing access to the Internet 140.

Remote network resources may also include one or more servers 150, 152, 154 that may provide various services, such as medical data updates, processing, storage and reporting. Such network resources may be provided with appropriate provisioning enabling secure access to medical data handled by the communication device 110. The servers 150, 152, 154 represent any number of available remote network resources, such as a server maintained by a medical practitioner or facility configured to collect medical data or resource allocation directives transmitted from the communication device 110.

Alternatively, the remote network resources may include data providers that supply data to the communication device 110, such as a weather service, pharmacy or other source of medical information. With access through the Internet 140, one primary server 150 may communicate directly with the other servers 152, 154 and have an exclusive connection to the communication device 110.

Alternatively, the various remote network resources may have alternative connection routes to the communication device 110 in order to provide redundancies. As with any resource, remote network resources may maintain and/or transmit to the connected communication device a medical mode override or a constraint value, which may be used to determine whether communication device 110 needs to switch to a medical mode.

Any of the servers 150, 152, 154 may include memory, processors and maintain its own database for storing or buffering data received from communication device 110. The servers 150, 152, 154 may also perform some analytics on received medical data, such as comparing data to threshold (i.e., alarm) settings to determine whether the communication device 110 should be placed in medical mode or whether any other urgent actions or alarms should be communicated to the patient or to healthcare providers. The servers 150, 152, 154 may also be configured with provisioning and device management software, data plan agreement management software, cellular operator connectivity interface functionality, cellular billing functionality, and customer support services. Unlike many other resources, each server may include various sub-resources, such as its own memory, processors, or means of communication that it uses to perform functions for the communication device. Thus, each server may maintain and/or transmit to the connected communication device a constraint value regarding its overall status or the status of any one of those sub-resources. Similarly, each server may transmit a medical mode override for placing the communication device in medical mode.

In an embodiment, the communication device 110 may serve not only as a conventional communication device, but also as a medical data gateway or hub for machine-to-machine (M2M) health care devices. In an embodiment, the system 100 may be configured such that an end-to-end encryption process leverages remote network resources, including data centers, and cloud services that allow electronic medical data to be exchanged securely and reliably with approved healthcare providers, payers, and patients using necessary protocols, such as those required for compliance with government rules and regulations. For example, medical data from the heart rate monitor 122 or wrist-worn device 124 may be conveyed through the communication device 110 to one or more remote network resources, such as the servers 150, 152, 154.

In an embodiment, when the communication device is in medical mode, an onboard or remote processor (i.e., a target resource) may be configured to temporarily save medical data in persistent storage before uploading it at scheduled times to a designated server. A data store module (DSM) resident on the onboard or remote processor may organize this stored data in a systematic way, store it persistently in a file system, and perform appropriate file housekeeping operations to manage the stored medical data. The tasks performed by the DSM may include storing medical data, triggering data transfers, monitoring file size (DSM may automatically trigger a transfer if the device's file size exceeds a pre-configured limit by checking the device file size during medical data writes to the file system and moving files as needed), checking for file aging (e.g., using appropriate parameters provided by the configuration manager the DSM may monitor the file system (using timers) for devices that don't send data for extended periods of time, and detect and promptly upload "aged" data files), maintain file system integrity (e.g., the DSM may keep track of the integrity of all created files by writing file names to a persistent list, monitoring this list, checking the list against the file system after reboots, and uploading discrepancies).

Figure 2:
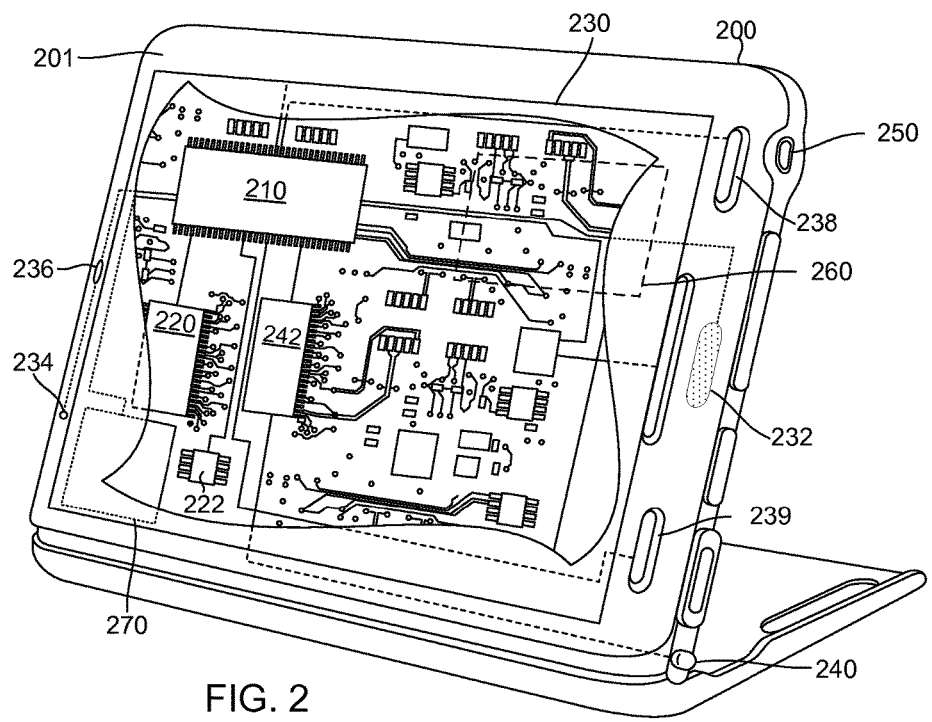
FIG. 2 is a component block diagram of a communication device suitable for use with various embodiments.

FIG. 2 illustrates a communication device 200 and various onboard resources contained within or directly attached to a permanent outer housing 201. For example, the communication device 200 may include a processor 210 coupled to internal memories 220 and 222, as well as additional processors, such as a dedicated processor and additional dedicated components 270 for medical data. Internal memories 220 and 222 may be volatile or non-volatile memories, and may also be secure and/or encrypted memories, or unsecure and/or unencrypted memories, or any combination thereof.

The processor 210 may also be coupled to various input and/or output components, such as a user interface, radio or communication port. User interfaces, such as touch screen display 230 (e.g., a resistive-sensing touch screen, capacitive-sensing touch screen, infrared sensing touch screen, or the like), speaker 232, microphone 234, camera 236, or physical buttons 238 and 239. Such a touch screen display 230 may be used to output a screen display or for receiving user input. However, the display of the communication device 200 need not have touch screen capability.

A radio of the communication device 200 may include one or more antenna 240 for sending and receiving electromagnetic radiation that may be connected to a wireless data link and/or cellular telephone transceiver 242 coupled to the processor 210. One or more communication ports may be provided, such as a Micro-B port 250 or the like, for connecting a data cable and communicating with peripheral devices or wired communication links. The number of communication ports may differ among the various embodiments depending upon the physical design of the permanent outer housing 201 and the particular market or application for which the communication device 200 is configured.

Additionally, the communication device may include a battery 260 as a power supply for other onboard resources. Alternatively, using a power cord the communication device 200 may be plugged-in to an external power supply, which may also be used to charge the battery 260.

A processor in the dedicated components 270 may be a medical mode processor, a medical mode SOC, or a medical mode core processor, used exclusively for managing medical data. In this way, specific and/or permanent components may be dedicated to medical data and to performing medical-related processing (e.g., processing data from medical sensors, determining medical conditions, reporting medical data. Also, such dedicated components 270 may be "hermetically sealed" from other components, meaning permanent restrictions are provided isolating the medical data from other data. Such dedicated components 270 may be medical grade components, providing security, privacy, and fulfilling regulatory compliance issues and requirements.

As with any resource, a constraint value for each onboard resource may be determined and maintained, which may be used to determine when the communication device is in medical mode to allocate resources. In this way, the constraint value may reflect when an onboard resource is strained, has conflicts, or is unavailable when that constraint value reaches a value of predetermined significance.

In an embodiment, the communication device may include an analysis and response module (ARM). The ARM may apply algorithms and other analytics to differentiate medical data from other data received by the communication device and/or allocate resources accordingly. The ARM may make context-dependent decisions on what algorithms and other analytics to apply to the received data based on various factors, such as the location of the communication device, input from one or more resources connected to the communication device, and/or other considerations. The ARM may also communicate with other communication device modules.

Figure 3:
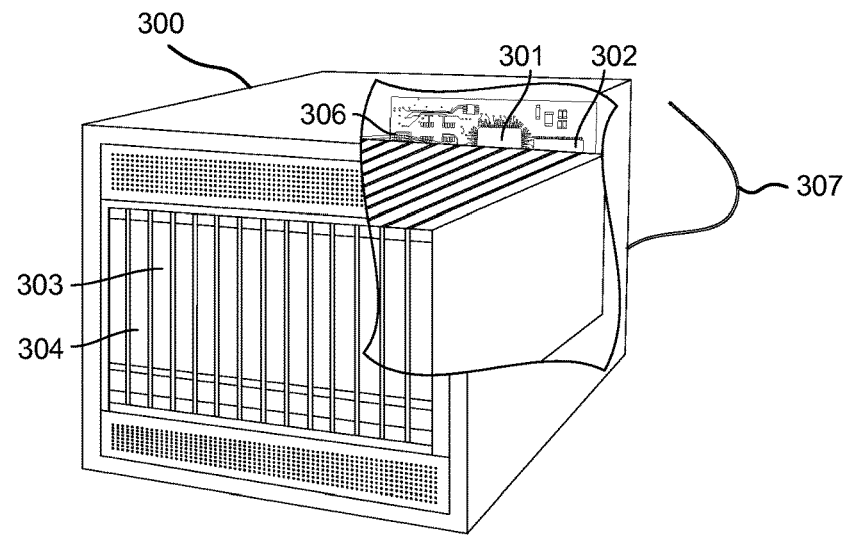
FIG. 3 is component block diagram of a server suitable for use with various embodiments.

FIG. 3 illustrates a server 300 that may be used as a remote resource in the various embodiments described above. Such a server 300 typically includes a processor 301 coupled to volatile memory 302 and a large capacity non-volatile memory, such as a disk drive 303. The server 300 may also include one or more removable disk drives 304, such as a floppy disc drive and/or a compact disc (CD) coupled to the processor 301. The server 300 may additionally include network access connections 307 coupled to the processor 301 for establishing data connections with network circuits, such as the Internet.

Figure 4:
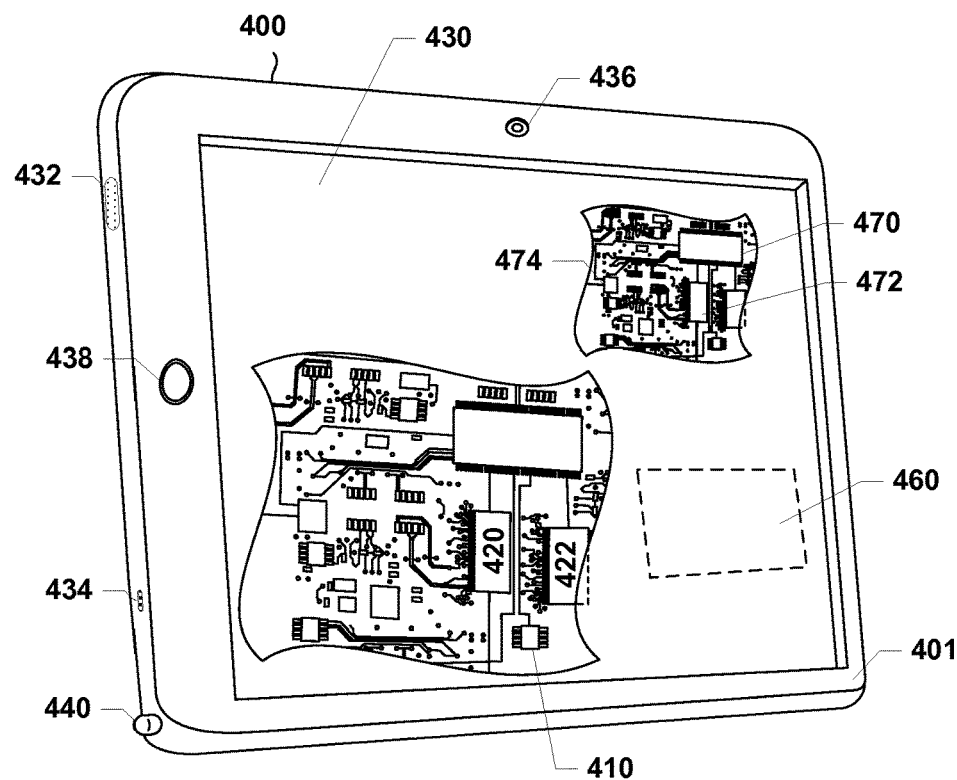
FIG. 4 is component block diagram of a tablet computer with dedicated resources suitable for use with various embodiments.

FIG. 4 illustrates another communication device in the form of a tablet computer 400 that may be implemented in and/or with any of the various embodiments. For example, the wireless device 400 may include a processor 410 coupled to internal memories 420 and 422. Internal memories 420 and 422 may be volatile or non-volatile memories, and may also be secure and/or encrypted memories, or unsecure and/or unencrypted memories, or any combination thereof.

The processor 410 may also be coupled to various input and/or output components, such as a user interface, radio or communication port. User interfaces, such as touch screen display 430 (e.g., a resistive-sensing touch screen, capacitive-sensing touch screen, infrared sensing touch screen, or the like), speaker 432, microphone 434, camera 436, or one or more physical buttons 438. Such a touch screen display 430 may be used to output a screen display or for receiving user input. However, the display of the tablet computer 400 need not have touch screen capability.

A radio of the communication device 400 may include one or more antenna 440 for sending and receiving electromagnetic radiation that may be connected to a wireless data link and/or cellular telephone transceiver coupled to the processor 410. One or more communication ports may be provided for connecting a data cable and communicating with peripheral devices or wired communication links. The number of communication ports may differ among the various embodiments depending upon the physical design of the permanent outer housing 401 and the particular market or application for which the tablet computer 400 is configured.

Additionally, the tablet computer 400 may include a battery 460 as a power supply (source) for the other resources. Alternatively, using a power cord the tablet computer 400 may be plugged-in to an external power supply, which may also be used to charge the battery 460. Any one of these elements are considered an onboard resource.

Further, the tablet computer 400 additionally includes various dedicated resources, including onboard processor 470, onboard memory 472, and backup power supply in the form of a supplemental onboard battery 474. Such dedicated resources may be used exclusively by and for managing medical data. The dedicated resources may also be reserved for use when the tablet computer 400 is in medical mode.

Each dedicated resource may individually be selected for use or more than one may be used as appropriate. These dedicated resources may be isolated from the open resources (i.e., non-dedicated resources) noted above that are not restricted from being used for other data outside medical mode. Additionally, the dedicated resources may be securely linked to one another, perhaps selectively exchanging data with the open resources. The dedicated resources may act as a medical subsystem of the communication device, which may not be impacted by software updates, viruses, or various changes to the open resources. In this way, the open resources also do not interfere with the operation of the dedicated subsystem. Such a subsystem may be configured and be compliant with government rules and regulations. In addition, to ensure medical data privacy, data retention, and security, the medical data may be tagged with identification information specific to the user, resources and any identified conditions or indications.

Aside from restrictions resulting from preferential allocation in accordance with the embodiments herein, the open resources may be freely used by the medical data and other data if desirable. In this way, a first processor, a first memory, a first radio, and a first power source may be open resources, while a second processor, a second memory, a second radio and a second power source may be dedicated resources of the communication device. Further, the dedicated memory may be an encrypted memory. The second processor, memory, and second power source may be separate and may not be accessible by the high-level operating system running on the device. Alternatively, the communication device need not have all those indicated dedicated resources or it may have additional dedicated resources.

In order to comply with rules or regulations imposed on medical equipment; the onboard and/or remote resources of the various embodiments may be "medical grade" resources. Medical grade resources may meet or be developed under standards that are required for medical equipment by health and/or regulatory authorities. For example, governmental authorities/agencies, such as the U.S. Food and Drug Administration and the European Commission Directorate General for Health and Consumers, may impose minimum standards on what may qualify as medical grade equipment. Such standards typically impose greater requirements for safety and reliability than commercial grade equipment due to the exigencies of medial use, particularly in life threatening situations. Additionally, such authorities/agencies may promulgate security and/or privacy rules, regulations and/or standards (i.e., HIPAA) imposing unique requirements on medical grade equipment for the storage and communication of patient and medical data. By providing medical grade resource components, the various embodiments enable multipurpose communication devices to be sold that are qualified to handle high priority medical data as well as non-medical data consistent with ordinary uses. Thus, in the various embodiments one or more of the dedicated resources may be a medical grade resource configured to act as a medical mode resource. For example, a medical mode processor or a medical mode SOC may be a medical grade device that complies with standards for medical devices.

Figure 5:
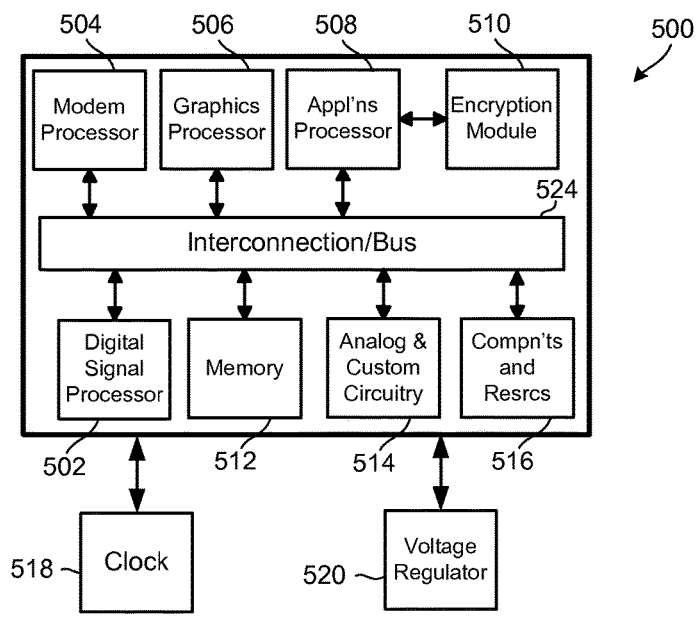
FIG. 5 is an architectural diagram of a system on chip suitable for use with various embodiments.

FIG. 5 is an architectural diagram illustrating an example system on chip (SOC) 500 architecture that may be used in a medical mode SOC that may be implemented within a variety of computing devices to provide such devices with the medical mode functionality of the various embodiments. The SOC 500 may include a number of heterogeneous processors, such as a digital signal processor (DSP) 502, a modem processor 504, a graphics processor 506, and an application's processor 508 configured for handling medical mode application processing. The SOC 500 may include a medical mode encryption module 510 that works with one or more of the heterogeneous processors 502, 504, 506, 508. A medical mode encryption module 510 may be an encryption module that is configured to implement encryption techniques that comply with regulatory requirements for protecting patient information and medical data. The SOC 500 may also include one or more coprocessors (e.g., a vector co-processor) connected to one or more of the heterogeneous processors 502, 504, 506, 508. Each processor 502, 504, 506, 508 may include one or more cores, and each processor/core may perform operations independent of the other processors/cores. For example, the SOC 500 may include a processor that executes a first type of operating system (e.g., FreeBSD, LINUX, OS X, etc.) and a processor that executes a second type of operating system (e.g., Microsoft Windows 8).

The SOC 500 may also include a dedicated memory 512 for storing medical data, such as patient information, sensor data, sensor history data, medical condition, doctors' orders or functionality selections, etc. Since medical data is subject to higher standards of privacy and government restrictions on collection/release (e.g., HIPAA), the memory 512 may be isolated from the rest of the device in which the SOC is installed by way of the SOC architecture. For example, the dedicated memory 512 may store medical data in memory partitions that are not generally accessible to non-medical applications. Also, medical data may be stored in encrypted format on the dedicated memory 512, or communicated between different chips within the device in encrypted format.

The SOC 500 may also include analog circuitry and custom circuitry 514 for managing medical sensor data, analog-to-digital conversions, wireless data transmissions, and for performing other specialized operations, such as processing encoded audio signals for games and movies. The SOC 500 may further include system components and resources 516, such as voltage regulators, oscillators, phase-locked loops, peripheral bridges, data controllers, memory controllers, system controllers, access ports, timers, and other similar components used to support the processors and other circuits on the SOC, enabling the SOC 500 to be dedicated to medical mode operations.

The system components 516 and custom circuitry 514 may include circuitry to interface with peripheral devices, such as cameras, electronic displays, wireless medical sensors, wireless-enabled medical devices, external transceivers, etc. The processors 502, 504, 506, 508 may be interconnected to one or more memory elements 512, system components, and resources 516 and custom circuitry 514 via an interconnection/bus module 524, which may include an array of reconfigurable logic gates and/or implement a bus architecture (e.g., CoreConnect, AMBA, etc.). Communications may be provided by advanced interconnects, such as high performance networks-on chip (NoCs).

The SOC 500 may further include an input/output interface circuit for communicating with resources external to the SOC, such as a clock 518 and a voltage regulator 520. Resources external to the SOC (e.g., clock 518, voltage regulator 520) may be shared by two or more of the internal SOC processors/cores (e.g., DSP 502, modem processor 504, graphics processor 506, applications processor 508, etc.).

The SOC 500 may also include hardware and/or software components suitable for collecting sensor data from medical sensors, user interface elements (e.g., input buttons, touch screen display, etc.), microphone arrays, sensors for monitoring physical conditions (e.g., location, direction, motion, orientation, vibration, pressure, etc.), cameras, compasses, GPS receivers, communications circuitry (e.g., Bluetooth®, WLAN, WiFi, etc.), and other well known components (e.g., accelerometer, etc.) of modern electronic devices. Additionally, the SOC 500 may be a "medical grade SOC," dedicated for handling medical data. The SOC 500 may also have stored in the memory 512 processor-executable instructions for configuring its medical-mode processor 508 to execute one or more of the embodiment methods of operating in a condition-appropriate medical mode, including allocating resources of a device in which the SOC 500 is installed as described herein. The SOC 500 may include a dedicated back up power supply, such as a small rechargeable battery (not shown). The SOC 500 itself, as well as individual hardware and/or software components thereof, may be considered a security resource, e.g., providing encryption and/or privacy protection capabilities, or even a necessary resource of a communication device. Thus, a resource status of the SOC 500 or individual components thereof may be considered when determining a resource allocation, such as when in medical mode.

The medical mode SOC 500 enables a wide variety of devices to be configured with medical mode capability/functionality simply by including the SOC in the device's circuitry. Implementing such an embodiment dedicated medical mode SOC 500 in a communication device also provides the dedicated processing, memory, communication and other resources that may be necessary to meet or comply with standards of safety, reliability and traceability, as may be required to meeting government licensing or other requirements established for medical equipment. By implementing the regulatory-compliance related components and software in an integrated SOC, this embodiment may simplify the design, production and licensing of communication devices that can perform regulated medical-related functions (e.g., monitoring and reporting of medical-related sensors and conditions). The medical mode SOC 500 may be dedicated hardware, working specifically when the device in which it is installed is in a medical mode of operation. Also, when in the medical mode of operation, the medical mode SOC 500 may work as a stand-alone system, may work with other hardware/software of the device in which it is installed, and may take over control of such other hardware/software.

Figure 6:
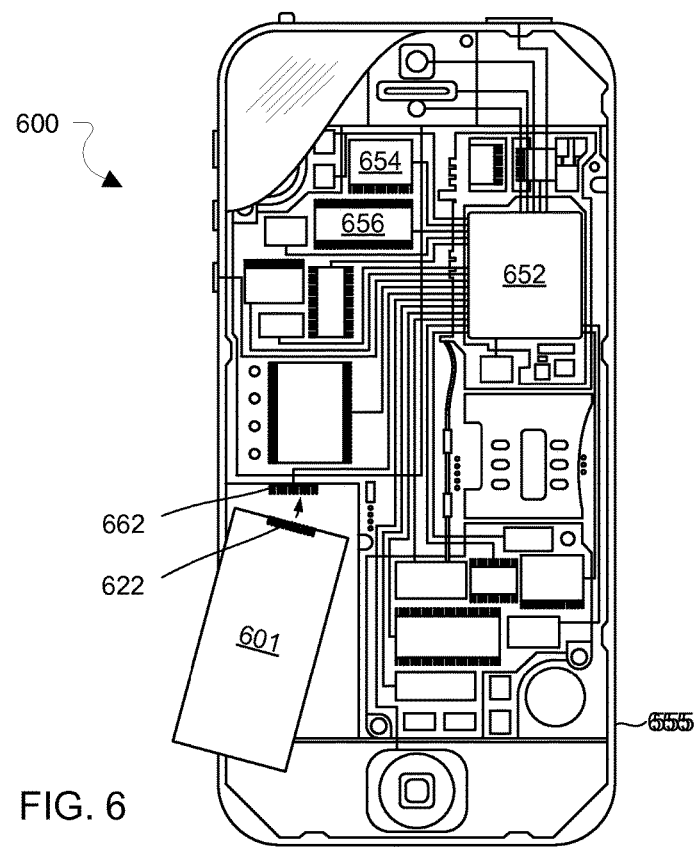
FIG. 6 is a component block diagram of a communication device including a removable system-on-chip suitable for use with various embodiments.

FIG. 6 is a component block diagram of a communication device 600 including a removable medical mode SOC 601. The removable medical mode SOC 601 may be implemented within a variety of computing devices to provide such devices with the medical mode functionality of the various embodiments. As with the medical mode SOC 500 of FIG. 5 described above, the removable medical mode SOC 601 may include its own hardware and/or software components, such as processor(s), memory and/or power. Such hardware and/or software components may be similar and/or redundant to other hardware or software components of the communication device 600, which may include a processor 652, a user interface controller 654, and internal memory 656. The communication device 600 may include a device connection interface 662 for coupling to a chip connection interface 622 of the removable medical mode SOC 601. The connection interface(s) 622, 662 may be singularly configured to accept one type of connection, or configured to accept various types of physical and communication connections, common or proprietary. The removable medical mode SOC 601 is illustrated in FIG. 6 as a component installed within the permanent outer housing 655 of the communication device 600. Alternatively, the device connection interface 662 may an external connection port for receiving the removable medical mode SOC 601 as an external/peripheral device, such as through a USB, FireWire, Thunderbolt, or PCIe connection. Removable medical mode SOC 601 can be a dedicated core of a CPU.

Figure 7:
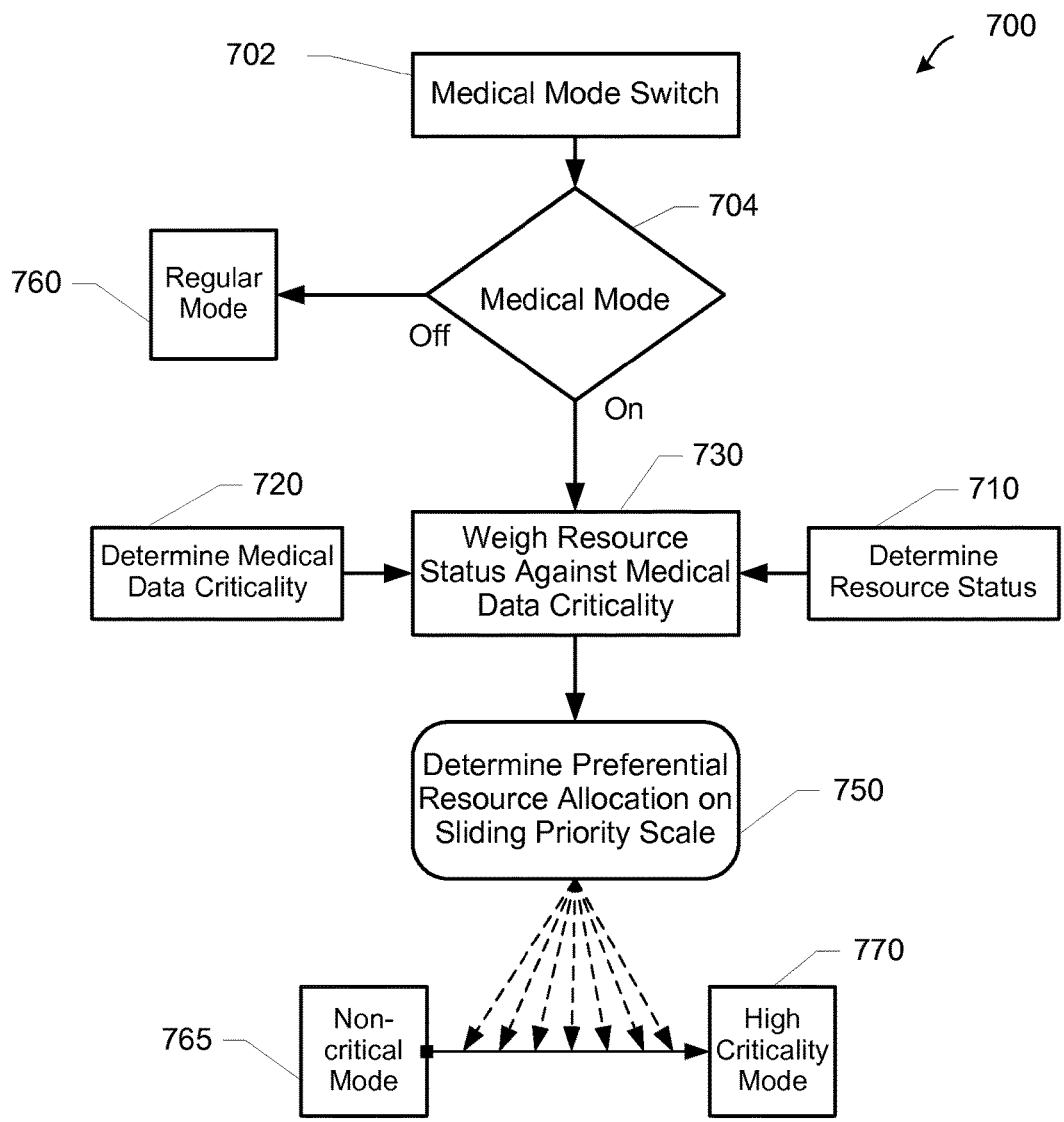
FIG. 7 is a process flow diagram illustrating an alternative embodiment method for allocating resources in response to receiving a medical mode override.

FIG. 7 illustrates an embodiment method 700 of managing a resource of a communication device that may be configured to process and communicate medical data in addition to other data. Allowing a communication device to initially determine whether to operate in a medical mode may eliminate, minimize and/or avoid any resource expenditures as compared to a scenario where the device operates in a medical mode by default.

In block 702, a signal may be received from medical mode switch that may be provided on the communication device. The medical mode switch may be a component of the communication device or part of a remote resource capable of communicating a medical mode override to the communication device. A processor of the communication device may thus receive a medical mode override, such as in the form of a signal from the medical mode switch, indicating whether the communication device should or should not operate in medical mode. A medical mode override directing the communication device into a medical mode of operation may be an "On-signal." In contrast, a medical mode override directing the communication device not to operate in a medical mode of operation (i.e., directing the communication device to operate in regular mode 760) may be an "Off-signal." In some embodiments, if the communication device is a dedicated medical communication device, the medical mode override directing the communication device into a medical mode of operation may be an always "On-signal" (e.g., preset or hardwired). Alternatively, if the communication device is a dedicated medical communication device, blocks 702 and 704 may be omitted from FIG. 7, and the device can operate solely in a medical mode. Such a device would find utility with practitioners or patients who are always in need of medical mode monitoring. By contrast, if the medical mode override is an always "Off-signal" (e.g., a factory setting), the communication device will be a device that solely operates in regular mode 760. For instance, such a device can simply operate as any contemporary communication device with no preferential treatment of medical data.

In some embodiments, as a component of the communication device itself, the medical mode switch may include a manual control accessible through a user interface of the communication device (e.g., an on/off button or a touch-screen icon). Such a manual control may allow a user, healthcare provider or other authorized individual to manually turn medical mode "On" or "Off" by interacting with the communication device through that user interface. The manual control may be incorporated into user settings of the communication device itself. In addition, the manual control may include advanced options, such as blocking or allowing other resources to act as a medical mode switch.

In addition to manual controls, various other resources may act as a medical mode switch, providing an On-signal, an Off-signal, enabling/disabling manual controls, or enabling/disabling automated controls. Persons skilled in the art will appreciate that resources can include onboard resources and/or remote resources, such as those described below providing information for determining medical data criticality with regard to FIG. 8. Thus, resources may generate or convey medical mode switch signals, including external/internal stimulus (e.g., commands, switches, connectors), software, network/component connections, data sources (e.g., sensor-based), periodicity or at least one temporal characteristic (e.g., time, frequency, etc.), location-based (e.g., using GPS, altitude, altimeter, pollen/pollution levels), healthcare decisions/directives, user activity (e.g., sleeping, awake, active, stressed), etc. In addition, an inference engine may consider various inputs for generating medical mode switch signals.

In some embodiments, the medical mode switch may be a control that automatically switches into a medical or regular mode based on input from various resources such as, for example, environmental data, context data, user settings, and/or any combination thereof. In some cases, an onboard resource of the communication device may signal a processor of the communication device to enter the medical mode. For example, user settings of the communication device may trigger a medical mode override in response to a critical resource constraint, such as an onboard battery being critically low. As a further example, a medical grade SOC may be configured to automatically signal a medical mode override when it is activated or in response to being installed in the communication device. Similarly, a remote resource may include a medical mode switch for remotely turning medical mode on or off at the communication device. For example, an authorized medical provider may transmit a signal activating medical mode after receiving test results. As a further example, an atmospheric sensor detecting conditions dangerous to a particular user, may remotely activate the medical mode by transmitting a signal recognized by an onboard processor of the communication device.

In other embodiments, the medical mode switch may be a control that switches into a medical or regular mode based on signaling from one or more resources (e.g., signaling embedded in a data stream) internal and/or external to the communication device. The signaling may include, for example, at least one of environmental data, context data, physiological and biological data, health record data, long-term historical data, directly input data, individual health risk data, population data, personal genomic data, behavioral data, public alerts, and/or any combination thereof. In embodiments in which more than one source may transmit/provide a medical mode switch signal, a hierarchy may be established for dealing with conflicting and/or redundant signaling. For example, a user's manual medical mode override may control medical mode determinations over all other resources. As a further example, a processor may cancel an input associated with a high pollen count, placing the communication device in medical mode, in response to receiving a directive from a physician who knows the user has taken allergy medications for a pollen allergy.

In determination block 704, the processor may determine whether a medical mode override is received directing the communication device into a medical mode of operation. In response to determining that a medical mode override Off-signal is received (i.e., determination block 704="Off"), the processor may maintain/switch the communication device to regular mode in block 760. In the regular mode, a processor of the communication device may apply no preferential handling to medical data or select resource allocations. In response to determining that a medical mode override On-signal is received (i.e., determination block 704="On"), the processor may weigh a resource status associated with a plurality of resources used by the communication device against a medical data criticality associated with the medical data managed by the communication device in block 730.

In block 710, the communication device may determine a status of at least one of a plurality of resources used by the communication device (i.e., a resource status). This determination may include resources currently in use and available, such as a processor, memory, network, power and/or security. In order to determine the resource status, a processor of the communication device may actively obtain the status information (i.e., receive a resource status in response to a request initiated by the processor) or passively obtained (i.e., receive a push notification from each resource or an intermediate source). The resource status of an individual resource may include a constraint value that represents either how much of a resource is available (e.g., quantity or rate) or how constrained a resource is relative to a lowest or normal level of constraint. For example, a percentage of available memory, battery charge, radio connectivity or processor load may each be considered a constraint value for those related resources. Also, the resource status may indicate whether the resource is available, or the condition of the resource (e.g., its readiness for use). Thus, the resource status determined in block 710 may indicate whether, how long, how much, at what level and/or at what rate the resource is or will continue to be available. Where a status of a plurality of resources is received, an individual status may be received for each of that plurality of resources.

In an embodiment, a critical resource constraint may be identified from a single resource status indicating a constraint value breaching a first constraint threshold for that resource. The first constraint threshold may be an individualized limit particular to the resource to which it applies. Additionally, a critical resource constraint may be identified when a combination of resource statuses indicate constraint values breaching individual second constraint thresholds of the respective resources associated with the combination of resource statuses. The second constraint thresholds may be different for each resource of the combination of resources. Also, each of the second constraint thresholds may be different from the first constraint threshold of the same resource. The difference between the first and second constraint thresholds may exist because of antagonistic combinations of critical resource constraints that may impair an ability of a communication device to handle medical data. In this way, two or more resources that may not individually meet their respective first constraint thresholds may together be identifiable to indicate a critical resource constraint because their constraint values both breach their more easily breached second constraint thresholds.

Each first constraint threshold may be a numerical value of predetermined significance chosen to reflect conditions associated with a resource in response to which priority may be given to medical data over other data based on the status of that particular resource. For example, a first constraint threshold for a battery of a communication device may be twenty five percent (25%) available power. Any level of power for that battery measured to be at or below twenty five percent (25%) may alone reflect a critical resource constraint. Such a constraint threshold may be chosen because it is associated with a level of power reserve needed for a particular period of time in which medical data is exclusively communicated or processed, or is projected to last long enough to take remedial actions such as seeking additional or alternative power.

Similarly, an available onboard memory capacity of ten percent (10%) may be designated as a first constraint threshold for onboard memory since roughly that capacity is needed as a reserve exclusively for storing or processing medical data. Thus, a measure of the available storage capacity of that memory indicating twenty three percent (23%) corresponds to that memory not having yet reached the first constraint threshold.

As a further example, a computational capacity of a processor or a software application (onboard or remote) may have a first constraint threshold associated therewith, such that when that value is breached a critical resource constraint exists (e.g., a central processing unit runs for more than a minute at 100% capacity).

Similar constraint thresholds may be determined for the connectivity level using a radio or the computational requirement thresholds needed to handle medical data. In this way, a resource may individually indicate a critical resource constraint exists by having conflicts, becoming too strained to fully handle medical data, running low, or somehow getting limited.

Additionally, a resource may be considered a "necessary resource," which refers to a resource that may be considered essential or needed to operate a particular function of the communication device and/or the communication device itself. Such a necessary resource may have a more easily breached constraint threshold than other resources. For example, a battery may be considered a necessary resource for a communication device to function in communication devices without an alternative power source. Similarly, in order to meet security/privacy requirements for handling confidential medical data, the availability of an encryption module or secure communication connection may be considered a necessary resource. Thus, a security level of such necessary resources may be further considered in determining whether a critical resource constraint exists.

Each second constraint threshold may be a numerical value of predetermined significance chosen to reflect conditions associated with a particular combination of resources in response to which priority should be given to medical data over other data based on the status of that particular combination of resources. For example, a second constraint threshold for a battery of a communication device may be thirty percent (30%) available power in combination with a second constraint threshold for a processor operating above ninety percent (90%) capacity for thirty seconds. Where both second constraint thresholds of the combination are breached, a critical resource constraint may be indicated to exist. The first constraint threshold for that same battery may be twenty five percent (25%) and for that same processor may be one hundred percent (100%) capacity for one minute. Thus, the second constraint thresholds for that battery and processor may both be breached without breaching one or either first constraint threshold.

Additionally, as noted above with regard to the processor constraint thresholds, a single constraint threshold may be associated with more than one value of predetermined significance to a single resource (e.g., a duration and capacity in the case of a processor). Thus, both values should exceed the designated constraint threshold in order to indicate the existence of a critical resource constraint. Further, a resource may have more than one type of critical resource constraint, and thus more than one constraint value for different aspects of the same resource. In this way, breaching either of those constraint values may be designated to separately indicate a critical resource constraint exists. For example, a processor may have a primary-first constraint threshold associated with processing capacity and a secondary-first constraint threshold associated with processing speed.

While both remote resources and onboard resources may indicate resource statuses, unlike onboard resources, the status of remote resources has a dependency on their connection to the communication device. The status of that connection, which connection is itself a resource, affects the status of the remote resource it connects. For example, a remote network server may become unavailable because that server itself is down, an intermediate remote resource is down (e.g., a remote network connection to that server), or an onboard resource is down (e.g., an onboard Wi-Fi connection used to reach that server is not working). Nonetheless, in determining whether a critical resource constraint exists, it may not matter why the status of a remote resource has breached a constraint threshold; just that it has. Alternatively, the method of managing a resource of a communication device may incorporate third constraint thresholds that take into account why the availability or condition of the remote resource has become significant.

In some embodiments, a transceiver engine or communication resource of the communication device may be configured to communicate with other resources (e.g., one or more devices or system-on-a-chip of one or more devices) to provide or receive information, instructions, or controls in the medical mode. For example, an appliance (e.g., a coffee maker or microwave) set up as a remote resource may communicate that it is turned on, but the communication device may determine that the user should not be using that appliance (e.g., determine that the user should not drink coffee or that the microwave may interfere with a surgical implant within the patient). Thus, a command may be transmitted via the transceiver engine to turn off the appliance before the user has had a chance to use the appliance. As another example, if a user used an appliance when communication between the appliance and the communication device has not been established (e.g., the communication device was not in the medical mode, the communication device was turned off, or the communication device was in another location), once the user connects to the communication device at a later time, the appliance can communicate to the communication device via the transceiver engine that the user had previously used the appliance. As a result, the communication device can perform one or more actions based on the receiving this communication (e.g., display an alert advising the user against drinking coffee or transmitting a message to a doctor's office).

In block 720, the medical data handled by the communication device may be checked to determine a criticality of the medical data (i.e., a medical data criticality), particularly the initiating medical data set. A medical data criticality may be determined from criticality indicators (i.e., direct or indirect) identified from the medical data. Also, the medical data criticality may take into account the resources needed for actions that need to be taken as a consequence of the criticality of the data and medical data itself. Various criticality indicators, as described below with regard to FIG. 8 may be used to determine a medical data criticality. A value associated with the criticality indicator establishes a weighting given to the medical data. If that criticality indicator value exceeds a predetermined value associated with the prioritizing data criticality, the medical data alone may establish a higher criticality mode.

In block 730, the communication device processor may weigh the resource status associated with a plurality of resources used by the communication device against a medical data criticality associated with medical data managed by the communication device. An inference engine may analyze resource status, criticality indicator(s) and the resources needed by the required actions and for managing the medical data.

In block 750, the processor applying the inference engine may determine a relative allocation of resources between "medical data" and its respective actions and the "other data" on a sliding priority scale. The sliding priority scale may define degrees of priority to be given to medical data over other data for one or more resources associated with the preferential allocation. As the sliding priority scale determination is made in block 750 in response to the communication device being in medical mode, it may start in a non-critical mode 765. Non-critical mode 765 may be a mode in which although resources are not allocated preferentially (e.g., the communication device is emulating a regular mode), the communication device is still capable of determining preferential resource allocation based on inputs received from one or more resources. The other end of the sliding priority scale may include the high criticality mode 770 in which the communication device processor can allocate a highest level of priority to medical data and its associated resources. The inference engine determination in block 750 may take into account the determined resource status from block 710 and the determined medical data criticality from block 720.

In some embodiments, additional remote resources (e.g., remote resources of FIG. 1) including storage and processing resources may be available to the communication device. In such embodiments, preferential resources allocated to medical data may include power resources needed to transmit one or more portions of medical data to a remote resource for remote storage or remote processing. In these embodiments, the communication device can allocate additional power resources for receiving the results of such remote processing from the remote resource. Consequently, determination of preferential resource allocation of block 750 may account for tradeoffs between resources that are locally available to the communication device and resources that are remotely available to the communication device (e.g., balance the need to leverage remote resources against available power resources on the communication device).

Figure 8:
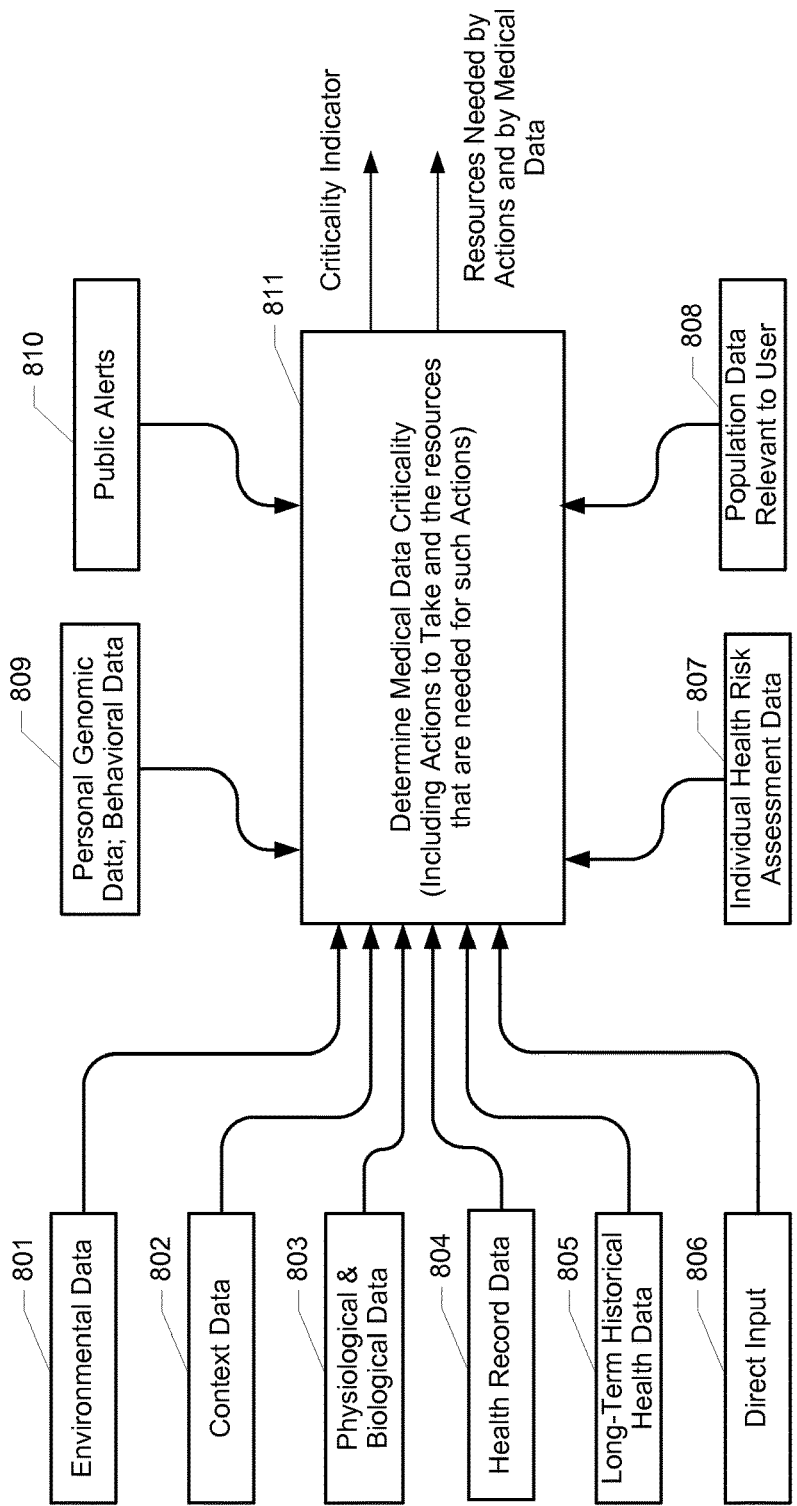
FIG. 8 is a process flow diagram illustrating an embodiment method for determining whether a medical data criticality exists.

An example of determining medical data criticality is shown in FIG. 8. In some embodiments, FIG. 8 may represent a more detailed view of the determining medical data criticality block 720 of method 700 (FIG. 7). Medical data criticality may be determined by combining or fusing, by an inference engine, a plurality of data associated with a user's condition, such as a multitude of different types of data (i.e., at least two different types of data) that are relevant to a user's condition and well-being. In some embodiments, the inference engine can combine or fuse both real-time and non-real time input data associated with a user in order to determine medical data criticality (e.g., data associated with a user's environment or context, or data belonging to a user).

Real-time input data can include any suitable type of real-time data associated with a user such as, for instance, environmental data 801, context data 802, physiological and biological data 803, any other suitable real-time input data, and/or any combination thereof. For example, environmental data 801, such as air quality, temperature, and/or humidity, may be used to determine the medical data criticality. Air quality and temperature may be important to an asthma patient. Further, medical data criticality may also depend on context of the user 802, e.g., geographical location of the user (i.e., GPS-based or altimeter), whether the user is resting, walking, running, or falling, inferred for example by sensors worn by the user or sensors on a wearable communication device. Additionally, medical data criticality can depend on physiological and biological data 803 obtained from sensors, such as from sensors worn on the body (e.g., heart rate and blood pressure data), sensors on-board the communication device or a remote sensor (e.g., a sensor communicating with the communication device through a short-range connection, such as Bluetooth®, or through a long-range connection, such as the Internet or a communications network.

Non-real time input data can include any suitable type of non-real time data associated with a user such as, for instance, health record data 804, long-term historical health data 805, personal genomic and behavioral data 809, any other suitable non-real time input data, and/or any combination thereof. For example, both long-term medical data 804, i.e., data from user's medical records (e.g., imaging, lab results, medications) and long-term historical health data 805, i.e., historical data from the user's body-worn sensors (e.g., weekly or daily averages of blood pressure measurements, weekly energy expenditure profile, daily average heart rate values, or heart rate variability) may be used in determining the criticality of the medical data. As another example, the inference engine can use personal genomic data and behavioral data 809 to determine the criticality of medical data. In some cases, genomic data 809 may be included in health record data 804.

Other types of input data associated with the user that can be used by the inference engine to determine medical data criticality can include individual health-risk assessment data of the individual 807, e.g., high risk for heart disease, and/or direct input 806. Direct input 806 provides direct, timely and current directives and inputs from healthcare professionals, caregivers of the user, or even the user themselves. The user may not feel so well that day, for example, and may have the means to input that information into the system. These types of data can be both real-time, non-real time, and/or a combination thereof.

In some embodiments, in addition to using input data associated with a user, the inference engine can use relevant data (e.g., real-time, non-real time, or a combination thereof) that are not associated with a user to determine medical data criticality. For example, the inference engine can use real population data from patients that are like the user 808. As another example, the inference engine can use public alerts 810, such as those from Centers for Disease Control (CDC), which are relevant to a specific user and that user's condition(s).

All this information may be used by an inference engine 811 to determine a medical data criticality. For example, interference engine 811 can generate a criticality indicator corresponding to the medical data criticality. The criticality indicator may then be provided to another component of the communication device and/or to a remote source.

In some embodiments, inference engine 811 can determine a resource requirement based at least in part on the medical data criticality. For example, inference engine 811 can generate an indication of at least one action to be taken. As another example, an estimate of the resources needed to successfully take these actions in a timely manner may be determined. Such information may then be used for determining a resource allocation in medical mode. For example, historical medically-relevant data and current medically-relevant data pertinent to a user may be considered to infer a criticality of medical data. Medically-relevant data, whether historical or current, may include any one or more of the above-noted types of data combined and/or fused by the inference engine 811.

As an example, inference engine 811 may observe and analyze data coming from body worn EKG and HR monitors and detect a rise in irregularity in heart rate above a predetermined threshold value. In some cases, inference engine 811 can detect a change, upon comparison, in the temporal characteristics of the EKG signal, e.g., its shape versus time, relative to the most recent historical EKG stored in long-term historical health data 805. As another example, inference engine 811 can poll the worn activity sensors data available from physiological & biological data 803 to determine that the user is currently at rest. However, inference engine 811 can determine from data in long-term historical health data 805 that the user was engaged in a higher level of physical activity in the last couple of hours immediately before being at rest. Moreover, health record data 804 may indicate that the user has a history of heart disease. The inference engine 811 can fuse this available information and infer that the user may be having a heart attack. Consequently, the inference engine 811 can change the value of the criticality indicator from a default low value to a high value.

In addition, inference engine 811 can identify the actions to be taken by the communication device, which in this example may include increasing the sampling rate of the EKG sensor from its default value to a higher value, transmitting alert messages to user's caregivers, starting to transmit the more frequently sampled EKG signals and heart rate information to user's cardiologist. The inference engine 811, in addition, may predict the critical battery and communication resources (e.g., bandwidth and latency of a wireless network that need to be established by the communication device) needed to successfully execute all these actions in the next critical hour and provide this information along with the criticality indicator as an output of block 720 of FIG. 7.

In some embodiments, the inference engine 811 may utilize a state machine (e.g., deterministic rule based and/or a statistical state machine) to analyze data, e.g., data from available resources such as 801-810, and infer decisions on medical data criticality and predict the critical resource requirements of actions that need to be taken in response to high medical criticality. The rule base and the statistical state machine of the inference engine may be trained off line, on-line, or partly off-line and on-line. In addition, the inference engine 811 may also exchange information with a clinical decision support system (CDSS) or knowledge support system (KSS), as described in the below, in determining the medical data criticality.

The inference engine 811 may be tied to the CDSS/KSS accessed as a remote resource and/or updated as an onboard resource. The CDSS/KSS may be an interactive system designed to assist physicians and other health professionals with decision-making tasks, such as determining a diagnosis based on patient data. The CDSS/KSS may link health observations with health knowledge to influence health choices by clinicians for improved health care. In this way, the CDSS/KSS may be an active knowledge system that uses a plurality of patient/user-related data to generate case-specific advice.

A processor may determine whether a received signal includes a direct criticality indicator, such as a medical mode signal, placing the device in the medical mode of operation. In response to medical data including a direct criticality indicator, the communication device will determine if an onboard analysis should be performed. The direct criticality indicator may be an identifiable code embedded in or added on to medical data. Also, the direct criticality indicator may be one of many codes associated with constraint values, which are weights given to medical data. The identification of one or more of such codes may trigger an indication of that is customized for the user if the value exceeds a predetermined prioritizing data criticality value.

A direct criticality indicator included in medical data, such as a medical mode signal, may come from one or more of various sources, such as an onboard or remote resource, a user, medical practitioner, caregiver, or other party. Resources may be configured to generate a direct criticality indicator continuously or in response to certain conditions being met. Also, the user may employ an application installed on the communication device in order to input a direct criticality indicator exceeding the prioritizing data criticality. Similarly, medical practitioners, caregiver, or agents associated with medical data management wanting to establish may transmit/input to the communication device a direct criticality indicator with a value exceeding the prioritizing data criticality. In this way, the user, medical practitioner, caregiver or agent(s) associated with the medical data may actively elect to force the communication device into a medical mode.

The presence alone of such a prioritizing data criticality may establish a particular set of data as requiring priority handling, and particularly a preferential allocation of resources. For example, a medical device (e.g., an EKG sensor or blood pressure sensor) transmitting readings (i.e., medical data) to the communication device may be configured to detect dangerous conditions and include a flag or alert message (i.e., a direct criticality indicator) in the data generated by that device. Similarly, resources measuring other elements or conditions, such as pollution levels, UV levels, and the presence of chemicals or other environmental conditions may trigger the transmission of an external input to the communication device in the form of a direct criticality indicator. If the criticality indicator exceeds the threshold associated with the prioritizing data criticality, the device may operate in medical mode based on information obtained from the medical data alone.

A processor may determine whether a direct criticality indicator is included in the medical data. In response to determining that a direct criticality indicator is included in the medical, the processor may make a further determination with regard to preferential resource allocation. In response to determining that no direct criticality indicator is included in the medical data, the processor may determine whether medical data may be processed by onboard resources to measure a medical data criticality from indirect indicators in the medical data. Additionally, the communication device may be designed with constraints on whom or what resources may transmit/input a direct criticality indicator to the communication device or place the device in medical mode. In this way, before receiving an input, and particularly before relinquishing control of whether the communication device operates in medical mode, a processor of the communication device may require a proper password, digital certificate, credentialing, and/or authorization.

In response to determining that no onboard resource is available for analyzing medical data or that no onboard process for analyzing medical data is compatible with a particular set of medical data needing this type of analysis, the processor may determine whether medical data may be analyzed by remote resources to ascertain whether a the communication device should operate in medical mode. In response to determining that an onboard resource is available for analyzing medical data, the medical data may be analyzed onboard. The analysis may also result in the generation of a message to a user, medical practitioners, or third parties. For example, the message may be an alert, an identification of an urgent medical issue or even a guideline for an appropriate medical response to the circumstance. Such messages may be displayed to the user using text or other visual indicators, output as an audible sound like an alarm or transmitted to a remote resource.

For example, an onboard processor may use algorithms and other analytics to analyze medical data based on the type of resource from which the data was received. In this way, data received from a glucose meter may be recognized in order to apply appropriate algorithms screening for Diabetes. Thereafter, a finding of Diabetes may be associated with a particular criticality indicator value, which value may be high enough to place the communication device in medical mode. Similarly, an onboard processor may determine that data is received from a cardiac monitor and may apply algorithms to screen for an arrhythmia, which may also generate an indirect criticality indicator. Such indirect criticality indicators measuring medical data criticality may be customized to a user of the communication device, particularly considering that individual's medical history, as well as current/recent medical readings and related information.

Additionally, context awareness may be built into the analysis of medical data for measuring medical data criticality. In this way, if a number of medically significant conditions are determined to coexist, an appropriate criticality indicator may be used, possibly reaching a prioritizing data criticality for the user of the communication device. For example, thresholds for pollen count, heart rate, blood sugar/pressure, glucose or other biometric readings or even a level of fluctuation or change in those values may be considered in the analysis of medical data and used to give a value to the criticality indicator. Also, medical data from multiple resources or separate sets of data from a single resource may be considered together in analyzing medical data to measure a medical data criticality. For example, the medical data may be analyzed by accessing historical data regarding the user, which may be compared or correlated to indirect criticality indicators.

Indirect criticality indicators may be identified through a look-up table, cross-correlation matrix, prioritization algorithm, or complex database functions associating key words, codes, or conditions with a value that may be treated as a criticality indicator. In this way, some text, characters, or even a series of symbols contained in the medical data may be matched to a code from a database that translates the information into an indirect criticality indicator for assigning a weight to the particular set of medical data.

In response to determining the communication device should operate in medical mode, the processor may determine a preferential resource allocation. In response to determining the communication device should not operate in medical mode, the processor may determine whether medical data may be analyzed by remote resources to ascertain whether a prioritizing data criticality is indirectly indicated in the medical data.

As an alternative, in response to indirectly determining the communication device should operate in medical mode, the processor may determine whether medical data may be further analyzed by remote resources to confirm whether a prioritizing data criticality is indirectly indicated in the medical data. Such an alternative provides a redundancy in establishing the existence of a prioritizing data criticality. Similarly, redundant onboard resources or multiple redundant remote resources may be employed to achieve more accurate results.

In response to determining that a remote resource is available for analyzing medical data, the medical data may be transmitted to that remote resource for processing. In response to determining that no remote resource is available for analyzing medical data or that no remote resource for analyzing medical data is compatible with a particular set of medical data needing this type of analysis, the communication device processor may be set to normal mode. In this way, no resource allocation preferential to medical data need be performed or any previously set resource allocations preferential to medical data may be removed (i.e., resources unrestricted for other data).

Medical data may be transmitted to a remote resource, such as a network server, to be analyzed. Once received by the remote resource, the medical data may be analyzed to identify indirect criticality indicators of a prioritizing data criticality. Similar to the analyzing onboard resources, remote resources may use algorithms and other analytics to perform on medical data being analyzed based on the type of resource from which the data was received. Also, remote resources may have access to enhanced processing power, more complex analytics and access to further resources not available or accessible to the communication device. Regardless, the remote analysis may attempt to identify indirect criticality indicators, particularly ones indicating a prioritizing data criticality. Also, indirect criticality indicators of prioritizing data criticality may be customized to a particular user of the communication device, considering that individual's medical history, as well as current/recent medical readings and related information. As a further example, context awareness may be built into the analysis of medical data for identifying indirect criticality indicators associated with a prioritizing data criticality. Also, medical data from multiple resources or separate sets of data from a single resource may be transmitted for remote processing for analyzing medical data to establish a prioritizing data criticality exists.

In normal mode, resource allocation preferential to medical data over other data need not be performed. Alternatively, a previous resource allocation preferential to medical data, corresponding to the same or related elements of data, may be removed or altered. For example, if an onboard processor was previously determined to be experiencing a critical resource constraint, that processor may have been allocated to only handle medical data because it is in medical mode. A subsequent determination that the same processor is no longer experiencing that critical resource constraint may warrant unrestricting that processor from managing other data. Similarly, previous preferential resource allocations may be changed or completely removed once the identified critical resource constraint or prioritizing data criticality is resolved (i.e., no longer identifiable).

In response to determining the communication device should operate in medical mode, a processor may determine a preferential resource allocation. The determination regarding which resource is the resource allocated preferentially for medical data may be based on what caused or contributed to the determination. Also, the determined resource(s) allocated preferentially may be based on the most extreme resource constraint or medical data criticality. An embodiment resource savings algorithm may make determinations with regard to the allocation of resources preferentially for medical data. When medical data is given priority, the use for other data of a selected resource of the communication device may be limited or restricted to ensure sufficient resources are available for management of medical data.

In response to determining the communication device should be in medical mode an onboard or remote processor may further access a database for guidance on the identified corresponding medical issue. In an embodiment, the database may provide details regarding actions a user or someone on behalf of the user should to take, warnings to display, medical providers to message or call, audibly or visibly output instructions, etc., in response to different identified medical issues. Also, based on a particular identified medical issue or condition, an onboard or remote processor may select a preprogrammed action to take. Further, the onboard or remote processor may provide guidance to a user on someone on behalf of the user, in the form of instructions on how to proceed to the nearest hospital, what medication to take or even simply an indicate that a medical provider is being called or informed of the circumstance. The warnings, indications and guidance may be presented in various manners, including flashing lights, text based messages on a display, video displays, audio indications, or any other indication perceptible to anyone in close proximity to the communication device. Also, an onboard or remote processor may notify authorities, physicians, family, etc., if indicated as an appropriate predetermined response based on the identified medical issue or condition. In addition, a transceiver or communication resource may communicate with other resources to provide information, instructions, or controls in response to switching into medical mode. For example, an appliance (e.g., a coffee maker or microwave) set up as a remote resource may communicate that it is turned on, but an inference engine may determine that the user should not be using that appliance (e.g., determine that the user should not drink coffee or that the microwave may interfere with a surgical implant within the patient), and thus a command may be transmitted to turn off the appliance.

At times, a medical practitioner, caregiver, or even a communication device user (i.e., the patient) may want or need to use the medical data managed by the communication device. For example, a medical practitioner or caregiver may want/need local access to the medical data when a network connection is lost or connectivity level is too low. The medical practitioner or caregiver may need access to the patient's medical history, vital signs, or trends in medical data, which may be collected and/or compiled by the communication device. Such access may be achieved directly through the communication device's user interface or through a device-to-device data link. Thus, with the proper authorization (i.e., complying with security and/or privacy standards/requirements) the medical practitioner or caregiver may be granted access to medical data or even yield control to the communication device entirely. Additionally, the communication device may maintain and/or transmit a record of such access by a medical practitioner or caregiver, making such access part of a medical history.

While various processor determinations are described in various embodiments as being performed in a particular order, it should be understood that the order may be changed and/or that more than may be performed before resources are allocated preferentially. Additionally, upon the determination either that a medical mode is turned on or off, an alert may be generated in order to advise a user or other external entity. Also, a record of the cause(s), timing, and implications of the device being placed in medical mode may be recorded in an onboard or remote memory, including one that is part of a database.

Figure 9:
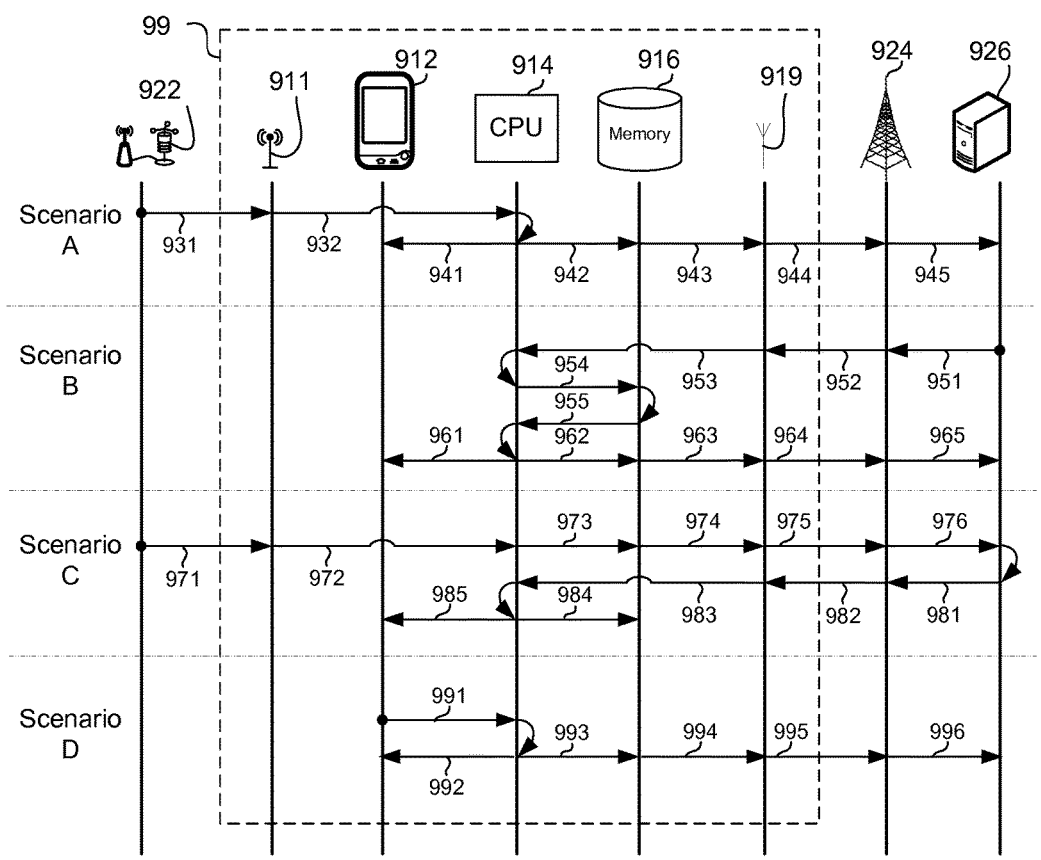
FIG. 9 is a communication flow diagram for various scenarios in accordance with various embodiments.

FIG. 9 illustrates communication flows in four different scenarios of how medical data is communicated between resources in the various embodiments. In the various scenarios, medical data is communicated between resources. Such medical data may include signaling information, identification codes, and other elements associated with the management of medical information, resources, and communications. While some resources simply pass that medical data along to another resource with little or no change in the medical data, other resources may alter the medical data significantly. Nonetheless, between each resource in the same scenario the medical data communicated is referred to with a different reference number, regardless of whether there is any substantial change in the medical data.

In Scenario A, the originating medical data starts from the peripheral sensor 922 that transmits the medical data 931 to a first onboard radio 911 of a communication device 910. The first onboard radio 911 may internally communicate the medical data 932 to a central processing unit (CPU) 914, which after processing communicates medical data 941 to the display of the user interface 912 and medical data 942 to an onboard memory 916. Additionally, the CPU 914 may communicate medical data 943 to a second onboard radio 919, which in-turn conveys medical data 944 to a long-range communication base station 924. The long-range communication base station 924 may communicate the medical data 945 to other base stations, through a further communication network, the Internet or the like until it reaches a remote network server 926. The communications in Scenario A may represent various situations. For example, Scenario A may represent a situation where sensor readings are transmitted from a peripheral sensor 972 to the communication device. Such readings may include a criticality indicator or other information. Once received and processed by the communication device, the user may be notified through a display of a user interface 912 and a medical provider may be notified through a remote network server 926.

In Scenario B, the originating medical data starts from the remote network server 926 that transmits the medical data 951 to the long-range communication base station 924. The long-range communication base station 924 may convey the medical data 952 to the second onboard radio 919, which may communicate medical data 953 to the CPU 914 that may process and/or analyze the data. The CPU 914 may communicate medical data 954 to an onboard memory 916 for storage and may receive medical data 955 from the onboard memory 916. Additionally, the CPU 914 may communicate medical data 961 to a display of the user interface 912 and enhanced medical data 962 again to the onboard memory 916. Further, the CPU 914 may communicate enhanced medical data 963 to the second onboard radio 919, which in-turn may convey medical data 964 to the long-range communication base station 924. The long-range communication base station 924 may communicate the medical data 965 through its various channels until it reaches the remote network server 926.

The communications in Scenario B may represent various situations. For example, Scenario B may represent a situation where after receiving updated information about a user, a remote network server 926 transmits that information to the communication device. The communication device recognizes that information as an indirect criticality indicator after comparing it to additional information in its own database. Thereafter, the user may be notified through the display of the user interface 912 and a medical provider may be notified through a remote network server 926.

In Scenario C, the originating medical data starts from the peripheral sensor 922 that transmits the medical data 971 to the first onboard radio 911 of the communication device 910. The first onboard radio 911 may internally communicate the medical data 972 to the CPU 914, which after processing may communicate medical data 973 to the onboard memory 916. Additionally, the CPU 914 may communicate medical data 974 to the second onboard radio 919, which in-turn conveys medical data 975 to the long-range communication base station 924. The long-range communication base station 924 may communicate the medical data 976 to the remote network server 926, which may further process the data. After processing, the remote network server 926 may transmit the medical data 981 to the long-range communication base station 924. The long-range communication base station 924 may convey the medical data 982 to the second onboard radio 919, which may communicate medical data 983 to the CPU 914 that may process, analyze, or simply receive the data. The CPU 914 may communicate medical data 984 to an onboard memory 916 for storage and communicates medical data 985 to a display of the user interface 912.

The communications in Scenario C may represent various situations. For example, Scenario C may represent a situation where sensor readings are transmitted from a peripheral sensor 972 through the communication device all the way to the remote network server 926. Such readings may include a criticality indicator identified by the remote network server 926 after analysis. The remote network server 926 may then transmit its results back to the communication device 910, so the user may be notified through the display of a user interface 912 and the information stored in the onboard memory 916.

In Scenario D, the originating medical data starts as an input from the user interface 912, which is communicated as medical data 991 to the CPU 914. The CPU 914 may communicate medical data 992 to a display of the user interface 912 and medical data 993 to the onboard memory 916. Further, the CPU 914 may communicate medical data 994 to the second onboard radio 919, which in-turn conveys medical data 995 to the long-range communication base station 924. The long-range communication base station 924 may communicate the medical data 996 through its various channels until it reaches the remote network server 926.

The communications in Scenario D may represent various situations. For example, Scenario D may represent a situation where a user decides to switch the communication device into a "medical mode," which means an override is entered (i.e., input). The communication device after allocating resources appropriately may indicate the medical mode state on the user display and notify the medical provider through the remote network server 926.

Figure 10:
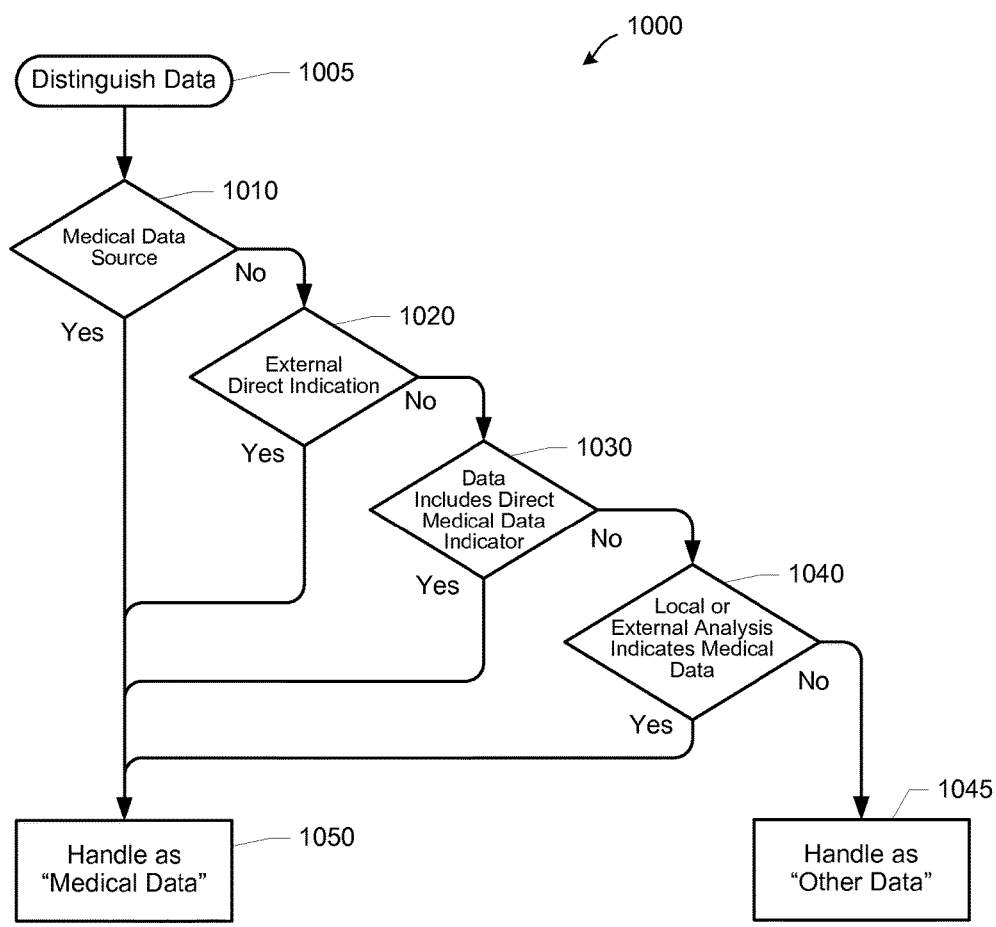
FIG. 10 is a process flow diagram illustrating an embodiment method for distinguishing data.

FIG. 10 illustrates an embodiment method 1000 for distinguishing medical data from other data. In block 1005, a processor of the communication device may initiate or continue the process of analyzing and thus distinguishing data, which may be performed continuously, periodically, selectively or otherwise. The determination regarding whether a particular set of data is or is not medical data may occur in direct response to the communication device being placed in medical mode. Alternatively and/or additionally, once data is determined to be medical data, it may contain one or more indicators, such as a criticality indicator indicating a prioritizing data criticality.

In determination block 1010, the source of the data being analyzed may be checked and/or used for a processor to determine whether the data coming from that source is or is not medical data. This is particularly applicable to sources of data that only handle medical data. For example, data coming from a medical sensor, like a heart monitor, may exclusively handle medical data and thus all data from that source may be considered medical data. In response to determining the data in question originated from a medical data source (i.e., determination block 1010="Yes"), in block 1050 that data may be treated by the processor as medical data. Otherwise, in response to not determining the data in question originated from a medical data source or it can be positively determined that the data came from a non-medical data source (i.e., determination block 1010="No"), in determination block 1020 the processor may determine whether a/an user/external medical data indication has been received.

In determination block 1020 the processor may determine whether an external direct medical data indication has been received, which may be from a user input or other external source. An external direct medical data indication represents and input that designates either all data or a particular set of data as medical data, regardless of what information that data contains. This type of indication may act as an override, even though the data being handled was from a non-medical source or did not contain any other medical data indicator. In response to determining an external direct medical data indication has been received (i.e., determination block 1020="Yes"), the processor may treat that data as medical data in block 1050. Otherwise, in response to determining that no external direct medical data indication has been received (i.e., determination block 1020="No"), the processor may determine whether the data itself includes a direct medical data indicator that it is medical data in determination block 1030.

Data handled by the communication device may include a direct criticality indicator that it is medical data. Such a direct criticality indicator may be a parameter or value embedded in the data that represents the direct criticality indicator. Additionally, such a parameter may also include a value used to prioritize different sets or types of medical data. In this way, a first type of medical data may be given priority over a second type of medical data. In accordance with a further aspect, a metric for medical data may be used to measure or determine how important the medical data is as compared to other data handled by the device, including other medical data.

Data including a direct criticality indicator that it is medical data is particularly applicable to sources of data that may not exclusively provide medical data. Alternatively, this technique may be used by a medical data source to denote and/or ensure data is handled as medical data. In response to determining that the data in question includes a direct medical data indicator (i.e., determination block 1030="Yes"), the processor may treat that data as medical data in block 1050. Otherwise, in response to determining that the data in question does not include a direct medical data indicator (i.e., determination block 1030="No"), the processor may determine whether a local or external analysis indicates the data is medical data, in determination block 1040.

In determination block 1040, the processor may look for an indirect criticality indicator that a particular set of data is medical data, which determination may be made locally at the communication device and/or from some remote resource. For example, an onboard process may apply algorithms and other analytics to the data to determine the data being handled is a heart rate pattern and generate an indication that such data is medical data. Alternatively, a remote source, such as a server operated by a medical provider, may analyze received data and generate an indication such data should be handled as medical data. In response to a local or external analysis indicating the data in question should be handled as medical data and such an indication is received (i.e., determination block 1040="Yes"), the processor may treat that data as medical data in block 1050. Otherwise, in response to determining that no external analysis indication is received or if a received analysis indicator reflects the data in question is not medical data (i.e., determination block 1040="No"), the processor may treat the data in question as "other data" (i.e., non-medical data) in block 1045. Alternatively, a local or remote analysis may conclude a particular set of data is in fact medical data, but not medical data warranting special handling, which may result in no medical data indication being reported.

Once a processor distinguishes medical data from other data and treats it distinctly as medical data in block 1050, it may allocate resources preferentially to that medical data; such as when in medical mode. In this way, the communication device may be configured to give priority to medical data processing and applications over other data. Also, a further analysis of the medical data handled in block 1050 may reveal a further indication of priority. For example, consider a situation where a remote source of data transmits a remote criticality indicator identifying its data as medical data, but the data itself includes a redundant indication in that regard.

In an embodiment, an onboard processor or remote processor may determine a context based on medical data received (e.g., location sensor data, accelerometer data, outdoor temperature data, clock inputs, etc.). The processor may use the determined context to modify and adapt the algorithms and other analytics applied to the medical data to tailor the results of the analysis and/or the actions taken in response to the results. As an example, an impending medical issue identified in a remote location may result in an alert being issued to a healthcare or emergency medicine provider.

In an embodiment, the medical data may be further divided into sets (i.e., distinct groups of data). Also, the sets of data may be designated to have a hierarchy of importance, so that a first medical data set can be higher in the hierarchy than a second medical data set.

When medical data is given priority when a communication device is in medical mode, a resource saving algorithm may allocate resources driven by the various factors. For example, a resource status, content of medical data and/or external direct indicator may raise the priority of medical data or cause the preferential allocation of resources.

An allocation of resources may occur in response to receiving a medical data input directing the communication device into a medical mode of operation. In response to determining that there is a critical resource constraint, a processor may determine whether one or more alternative resources are available that may take the place of the resource establishing the critical resource constraint. In response to determining that there is not a critical resource constraint, the processor may determine whether to prioritize data. In response to determining that an alternative resource is not available, the processor may determine a critical resource constraint allocation of one or more target resources. In response to determining that an alternative resource is available, a suitable available alternative resource may be designated by a processor for preferential handling of medical data. Suitable available alternative resource may include an onboard resource and/or a remote resource depending on the circumstance. For example, consider a scenario where an onboard memory almost full, as indicated by its constraint value well above its constraint threshold, such that medical data is diverted to a remote network memory location for storage. As a further example, consider a scenario where a remote processor is busy already processing a first set of medical data (i.e., straining to process further medical data handled by the communication device, as indicated by a high constraint value), which triggers a medical mode of operate such that a second set of medical data is diverted to an onboard processor for processing locally. In this way, medical data may be diverted to the alternative resource for handling. Also, any related resources may be updated to facilitate the selected alternate resource taking over or assisting in the management of medical data.

A processor may determine a sliding scale resource allocation based on the conditions triggering the weights given to the resource constraint value(s) and the medical data criticality indicator(s). For example, an embodiment resource saving algorithm may partially divert resources to support the management of medical data along a sliding scale that balances resource availability against the safety and efficacy requirements of the medical application (for example, 20% of CPU and 50% of bandwidth for medical data, increasing to 100% as resources become more constrained). In this way, diverting medical data to a remote resource or an onboard resource of the communication device may be part of allocating resources preferentially.

The determinations regarding which resource(s) may be allocated preferentially for medical data may result from an inference engine executed by a local processor, or possibly a remote processor, that identifies such resources under various scenarios. Such an inference engine may be able to consider a broad range of conditions, the resource status of one or more available resources and other relevant information. For example, a particular resource, such as an onboard processor, may be restricted from being used for other data. In this way, when in medical mode no data that is not considered medical data may be processed by that onboard processor. Alternatively, the restrictions may be limited, so that in the same example the processor may be used for other data to a limited extent, such as twenty percent (20%) of processing capacity. In this way, a predetermined portion of the resource is made available to ensure medical data is managed appropriately. There may even be conditions in which resources generally reserved as dedicated resources exclusively for medical data are allowed to be used to a limited extent for other data.

Another scheme of resource allocation may simply give precedence to medical data over other data. In this way, if little or no medical data is being managed by the communication device then few or no restrictions are placed on the other data. If the communication device suddenly receives a substantial amount of medical data, the medial data may be given precedence over the other data, so the other data must wait to be processed.

An alternate resource may simply take the place of the resource with the critical resource constraint. Also, more than one resource may be needed to take the place of the constrained resource. Thus, the circumstance and the resource status of the alternate resource may be taken into account when the processor determines the allocation level. The resource allocation determination may be resource-based (i.e., triggered from a critical resource constraint being identified). Thus, the inference engine may have predetermined designations for which resource(s) will be used under such circumstances. For example, a radio, processor, memory, and/or power source may be designated for use in the event of a resource-based medical mode, where no alternative similar resource is available. The inference engine may be programmed to handle various circumstances relating to a critical resource constraint. Also, special actions may be taken under certain circumstanced relating to particular critical resource constraints. Such actions may be controlled by an inference engine programmed with predetermined responses to various circumstances. For example, where the primary and/or back-up power source(s) for the communication device is/are critically low, once that power is exhausted all onboard resources of the communication device will become unavailable unless additional power is obtained. Thus, the communication device may be configured to alert a user, medical provider or other entity, through text or other visual message, such as lights flashing/blinking and/or an audio signal. In this way, before the communication device uses its last bit of remaining power (i.e., a virtual dying breath), a distress signal may be output or transmitted to the user, other entity, and/or a remote source. Similarly, a user, other entity, and/or a remote resource may be notified of other critical resource constraints. The notification may even include a location of the communication device, such as an address or global positioning system coordinates. Under select circumstances, the remote resource may redirect medical data normally sent to the communication device, to another remote resource. Additionally, such an inference engine may be reconfigurable, so the actions may be customized or changed as needed.

The resource allocation determination may be based on a prioritized data criticality (i.e., triggered as a result of a criticality indicator). Thus, the inference engine may take into account the prioritized data criticality and use particular predetermined designations for what resource(s) will be affected under such circumstances. For example, a radio, processor, memory, and/or power source may be designated to be allocated preferentially for medical data when operating in medical mode. Once the resource(s) for allocation is/are determined, the level of preferential treatment for each resource may be determined by the processor. Such preferential treatment may be a priority that may include exclusivity, which is given to medical data over other data. Also, the preferential treatment may have limits (e.g., some percentage of bandwidth, processing capacity, memory usage or power consumption) so the use of the target resource is not completely taken over by the medical data. Thereafter, the processor may determine whether further resource allocation is needed.

The resource allocation determination may be a result of weighing both the resource status and the medical data criticality. The communication device may be operating in medical mode in spite of the fact that neither a critical resource constraint nor a prioritizing data criticality was established. In this case, a sliding scale may be used that further takes into account the weight given to the resource status and the medical data criticality respectively. Also, predetermined designations of resource allocations may be established for various scenarios along the sliding scale, with one end of the scale more heavily influence by the resource status and the other end of the scale influenced by the medical data criticality.

In response to resource allocations being designated/determined, the processor may determine a level of allocation that is appropriate and particularly suitable for the situation. For example, consider a circumstance where reception through a cellular radio is lost for whatever reason. The cellular radio in the communication device may trigger a medical mode of operation based on the lack of connectivity or too low a connectivity level. Without an alternative radio to communicate medical data, all medical data must be diverted, for example to an onboard processor and/or memory, until a cellular communication connection resumes. In this way, the communication device that has lost connectivity may work to collect and store medical data until it gains a connection or for more direct retrieval from onboard memory.

The level of allocation that is needed may depend upon the determined circumstances. For example, a determination may be made regarding whether priority or possibly exclusivity needs to be given to the medical data with regard to a particular designated resource. Such priority/exclusivity may not be necessary if the use of the alternative resource, taking over for a constrained resource, can handle both medical data and other data. For example, consider a remote network resource, such as a telecommunications provider's server, that has gone down and is unavailable, but an alternative redundant server is available for use by the communication device. Under such a circumstance, no priority need be given to the handling of medical data and all data handling to the remote server may be redirected to the alternative server.

Preferential treatment by a resource of medical data over other data may include a full priority, limited priority, or even exclusivity. Thus, the preferential treatment may have limits (e.g., some percentage of bandwidth, processing capacity, memory usage or power consumption) so the use of the target resource is not completely taken over by the medical data. For example, data that is handled by the communication device and determined to be medical data may get first priority over other data to resources such as radios, processors, memory, and power. First priority means the medical data gets processed, transmitted and/or stored before contemporaneous other data. Alternatively, a predetermined percentage of one or more resources may be reserved for use in handling medical data, but the resource may otherwise be used for handling other data. Similarly, a first priority may be applied only to a predetermined percentage of a target resource. Regardless, once a level of allocation is determined, the processor may determine whether further resource allocation is needed.

Optionally, the processor may monitor the device's state (e.g., battery level, signal strength, etc.), as well as information about the user's condition (e.g., sensor data or activity that could have a medical implication) to watch for changes in the conditions that would (e.g., by changing by more than a threshold amount) suggest the device should operate in or out of medical mode. For example, when the communication device is in a medium priority medical mode of monitoring and transmitting a patient's heart rate or blood sugar readings, a sudden accelerometer reading and/or a voice recognition algorithm detecting the user crying for help, as might be consistent with the person falling, may indicate that the current medical mode resource allocation is not appropriate for the changed conditions. As another example, the processor may determine that the battery is being drained in the current resource allocation mode, and determine that a new resource allocation is required in order to ensure continued patient monitoring/reporting of the most critical parameters while extending the time the device will operate on the battery. In response to the processor determining that the device's or the user's condition(s) have changed resource allocation process by again be initiated by the processor. In this manner the communication device can react to changes in conditions in order to achieve the proper resource allocation responsive to changes in the user's and the device's current conditions.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular. Further still, the word "plurality" is intended herein to refer to more than one element. A plurality may include as few as two elements, a large number of elements, or any number in between. The word "exemplary" is used herein to mean "serving as an example, instance, or illustration." Any implementation described herein as "exemplary" or an "example" is not necessarily to be construed as preferred or advantageous over other implementations. Additionally, use of the words "first" and "second" or similar verbiage is intended herein for clarity purposes to distinguish various described elements and is not intended to limit the claims to a particular order or hierarchy of elements. For example, as used in the claims the terms "first onboard resource," "second onboard resource," and "third onboard resource" may refer to the same or distinct onboard resources. Similarly as used in the claims, the expressions "first part of the medical data" and "second part of the medical data" may refer to the same or distinct parts of the medical data.

As used herein, the terms "computer," "tablet computer" and "computing device" refer to any programmable computer system that is known or that will be developed in the future. A computer system may be configured with software instructions to perform the processes described herein.

As used herein, the terms "component," "module," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

Communication devices generally include various types of electronic hardware (also referred to as simply "hardware") that consist of interconnected physical electronic components, which perform operations. Hardware may include onboard components, such as a sensor, display, processor, memory, radio, power source, interface and other peripheral components. Often a battery is used as a power source, but the various embodiments consider remote and onboard sources of power to be power sources in terms of resources, if available at some point to the device. For example, a wired electrical connection to an electrical outlet may be a remote power resource and other internal or external resources, such as solar cells, may be an onboard power resource.

Additionally, communication devices may include one or more of various types of radios, each of which may be considered a resource. A radio may be used to communicate with remote network elements such as through a telecommunications network, as well as local resources such as sensors or data collectors in close proximity to the device. As used herein, the term "radio" refers to one or more components used for the wireless transmission and/or reception of signals, for example by means of electromagnetic waves. Various forms of data, including audio, video, text and more may be communicated using a radio. The data communicated using a radio may be extracted and transformed back into its original form. A radio may include a transmitter and/or receiver using one or more of various technologies and/or protocols, such as cellular, global positioning system (GPS), Wi-Fi, Bluetooth®, ANT, ZigBee and the like.

The processor(s) in the various embodiments, which may be considered a resource, may be any programmable microprocessor, microcomputer, controller, microcontroller, state machine or multiple processor chip or chips that can be configured by software instructions (applications) to perform a variety of functions, including the functions of the various embodiments described herein. In some devices, multiple processors may be provided, such as one processor dedicated to wireless communication functions and one processor dedicated to running other applications. A processor may be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Also, the hardware used to implement the various illustrative logics, logical blocks, modules, and circuits described in connection with the embodiments disclosed herein may be implemented or performed with a processor. Alternatively, some steps or methods may be performed by circuitry that is specific to a given function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

If implemented in software, the functions may be stored as one or more instructions or code on a non-transitory computer-readable medium or non-transitory processor-readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Typically, software applications may be stored in the internal memory before they are accessed and loaded into the processor. In some communication devices, the processor may include internal memory sufficient to store the application software instructions. In some devices, secure memory may be dedicated in a separate memory chip coupled to the processor. In many devices, the internal memory may be a volatile or nonvolatile memory, such as flash memory, or a mixture of both. For the purposes of this description, a general reference to memory refers to all memory accessible by the processor, including internal memory removable memory plugged into the device, and memory within the processor itself.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method of managing resources of a communication device, the communication device configured to process and communicate medical data in addition to other data, the method comprising:
    determining whether to switch from a first mode of operation to a medical mode based on at least one signal;
    switching to the medical mode in response to determining to switch to the medical mode;
    weighing a resource status associated with a plurality of resources used by the communication device against a medical data criticality associated with the medical data managed by the communication device in response to switching to the medical mode;
    determining a degree of priority, along a sliding priority scale, that a resource of the plurality of resources allocates to support handling the medical data over the other data based on the weighing of the resource status against the medical data criticality, wherein use of the resource for the other data is limited, based on the determined degree of priority, to the extent that use of the resource for the medical data competes with the use of the resource for the other data; and
    setting the resource to give the determined degree of priority to support handling the medical data over the other data.

2. The method of claim 1, further comprising:
    distinguishing the medical data from the other data.

3. The method of claim 1, wherein the at least one signal is one of an on-signal and an off-signal.

4. The method of claim 1, wherein the at least one signal is a preset signal or hardwired signal directing the communication device to operate in the medical mode.

5. The method of claim 1, wherein the determining whether to switch is based on one of:
  a manual control;
  a first processor control that automatically switches into the medical mode or a regular mode based on input from the plurality of resources;
  a second processor control that switches into the medical mode or the regular mode based on signaling from the plurality of resources; and
  a factory setting.

6. The method of claim 1, wherein weighing the resource status is performed by a remote resource separate from the communication device.

7. The method of claim 1, further comprising at least one of:
  diverting at least a first part of the medical data to a first onboard resource of the communication device; and
  diverting at least a second part of the medical data from a second onboard resource to a remote resource of the communication device.

8. The method of claim 1, further comprising at least one of:
  ensuring a predetermined portion of use of the resource is available for managing the medical data; and
  ensuring the medical data has precedence over the other data with regard to the use of a third onboard resource of the communication device.

9. The method of claim 1, wherein setting the resource to allocate the determined degree of priority includes dedicating the resource exclusively to managing the medical data and preventing the resource from being used for the other data.

10. The method of claim 1, wherein setting the resource to allocate the determined degree of priority includes diverting the medical data to the resource, wherein the resource is a dedicated resource used exclusively for managing the medical data.

11. The method of claim 1, wherein setting the resource to allocate the determined degree of priority includes preventing the plurality of resources from being used for managing the other data.

12. The method of claim 1, further comprising:
  activating a dedicated resource in response to determining to switch to the medical mode, wherein the dedicated resource is used for the medical data and restricted from being used for the other data.

13. The method of claim 12, wherein the activated dedicated resource is used for the other data to a limited extent based on a combined weighting given to the resource status and the medical data.

14. The method of claim 12, wherein the activated dedicated resource is a system on chip (SOC) onboard the communication device.

15. The method of claim 14, wherein the SOC is a medical grade SOC.

16. A communication device configured to process and communicate medical data in addition to other data, the communication device comprising:
  a memory; and
  a processor coupled to the memory, wherein the processor is configured with processor-executable instructions to perform operations comprising:
    determining whether to switch from a first mode of operation to a medical mode based on at least one signal;
    switching to the medical mode in response to determining to switch to the medical mode;
    weighing a resource status associated with a plurality of resources used by the communication device against a medical data criticality associated with the medical data managed by the communication device in response to switching to the medical mode;
    determining a degree of priority along a sliding priority scale that a resource of the plurality of resources allocates to support handling the medical data over the other data based on the weighing of the resource status against the medical data criticality, wherein use of the resource for the other data is limited, based on the determined degree of priority, to the extent that use of the resource for the medical data competes with the use of the resource for the other data; and
    setting the resource to give the determined degree of priority to support handling the medical data over the other data.

17. The communication device of claim 16, wherein the memory and the processor are coupled and integrated together on a system on chip (SOC).

18. The communication device of claim 17, further comprising at least one of:
  a radio coupled and integrated on the SOC; or
  a power source coupled and integrated on the SOC.

19. A non-transitory processor-readable storage medium having stored thereon processor-executable instructions configured to cause a processor of a communication device, coupled to a memory, to perform operations for processing and communicating medical data in addition to other data comprising:
  determining whether to switch from a first mode of operation to a medical mode based on at least one signal;
  switching to the medical mode in response to determining to switch to the medical mode;
  weighing a resource status associated with a plurality of resources used by the communication device against a medical data criticality associated with the medical data managed by the communication device in response to switching to the medical mode;
  determining a degree of priority along a sliding priority scale that a resource of the plurality of resources allocates to support handling the medical data over the other data based on the weighing of the resource status against the medical data criticality, wherein use of the resource for the other data is limited, based on the determined degree of priority, to the extent that use of the resource for the medical data competes with the use of the resource for the other data; and
  setting the resource to give the determined degree of priority to support handling the medical data over the other data.

20. A method of managing resources of a communication device, the communication device configured to process and communicate medical data in addition to other data, the method comprising:
  receiving, at an inference engine of the communication device, the medical data associated with a user's condition;
  determining, using the inference engine, a medical data criticality by combining different parts of the medical data;
  determining a degree of priority along a sliding priority scale that a resource of the plurality of resources allocates to support handling the medical data over the other data based on weighing a resource status associated with a plurality of resources used by the communication device against the medical data criticality, wherein use of the resource for the other data is limited, based on the determined degree of priority, to the extent that use of the resource for the medical data competes with the use of the resource for the other data; and setting the resource to give the determined degree of priority to support handling the medical data over the other data.

21. The method of claim 20, wherein the different parts of the medical data are associated with at least two different types of data.

22. The method of claim 20, wherein the medical data comprises at least one of environmental data, context data, physiological and biological data, health record data, long-term historical health data, directly input data, individual health risk data, personal genomic data, behavioral data, or public alerts.

23. The method of claim 20, further comprising:
changing a criticality indicator corresponding to the medical data in response to determining the medical data criticality.

24. The method of claim 23, wherein the generating the criticality indicator comprises:
comparing long-term historical health data associated with a patient with at least one temporal characteristic obtained from a sensor attached to a user;

detecting a change in the at least one temporal characteristic; and changing the criticality indicator from a default low value to a high value.

25. The method of claim 24, further comprising providing the criticality indicator to one of the plurality of resources of the communication device.

26. The method of claim 24, further comprising providing the criticality indicator to a remote resource.

27. The method claim 24, further comprising generating an indication of at least one action to be taken.

28. The method of claim 20, further comprising:
determining a necessary resource for completing at least one action during a particular period of time; and determining a resource allocation in a medical mode based on the determined necessary resource.

29. The method of claim 20 further comprising exchanging information associated with the medical data criticality with at least one of a clinical decision support system or a knowledge support system.

30. The method of claim 20, wherein at least one of determining the medical data criticality or determining a resource requirement of actions that need to be taken in response to a high medical criticality being determined is performed using a state machine.

* * * * *